United States Patent
Sinha et al.

(10) Patent No.: US 8,404,724 B2
(45) Date of Patent: Mar. 26, 2013

(54) UNIT DOSE FORMULATIONS AND METHODS OF TREATING THROMBOSIS WITH AN ORAL FACTOR XA INHIBITOR

(75) Inventors: Uma Sinha, San Francisco, CA (US); Stanley J. Hollenbach, South San Francisco, CA (US); Keith Abe, South San Francisco, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 1074 days.

(21) Appl. No.: 11/999,957

(22) Filed: Dec. 7, 2007

(65) Prior Publication Data
US 2008/0153876 A1 Jun. 26, 2008

Related U.S. Application Data

(60) Provisional application No. 60/873,792, filed on Dec. 8, 2006, provisional application No. 60/947,629, filed on Jul. 2, 2007.

(51) Int. Cl.
*A61K 31/4402* (2006.01)

(52) U.S. Cl. ......... 514/352; 514/822

(58) Field of Classification Search .......... None
See application file for complete search history.

(56) References Cited

U.S. PATENT DOCUMENTS

| 5,153,176 | A | 10/1992 | Abe et al. |
| 6,376,515 | B2 | 4/2002 | Zhu et al. |
| 6,635,657 | B1 | 10/2003 | Beight et al. |
| 2002/0002183 | A1 * | 1/2002 | Zhu et al. |
| 2007/0112039 | A1 * | 5/2007 | Grant et al. |

FOREIGN PATENT DOCUMENTS

| WO | WO 02/18623 | 3/2002 |
| WO | WO 02/26731 | 4/2002 |
| WO | WO 2007/056517 | 5/2007 |

OTHER PUBLICATIONS

Berge et al., Journal of Pharmaceutical Sciences, 1977, vol. 66(1), pp. 1-19.*
Toutain et al., "Species Differences in Pharmacokinetics and Pharmacodynamics" in: Handbook of Experimental Pharmacology: Comparative and Veterinary Pharmacology, 2010, pp. 20-48.*
Zhang et al., "Design, synthesis, and SAR of anthranilamide-based factor Xa inhibitors with improved functional activity," Bioorganic & Medicinal Chemistry Letters, Oxford, GB, vol. 14, No. 4, 2004, pp. 989-993, XP002414600.
Zhu et al., "Inhibitory effect of carboxylic acid group on hERG binding," Bioorganic & Medicinal Chemistry Letters, Oxford, GB, vol. 16, No. 21, Nov. 1, 2006, pp. 5507-5512, XP005663480.
Zhang, et al., "Design, synthesis, and SAR of anthranilamide-based factor Xa inhibitors incorporating substituted biphenyl P4 motifs," Biorganic & Medicinal Chemistry Letters, vol. 14, No. 4, Feb. 23, 2004, pp. 983-987, XP002471265.
International Search Report for PCT/US2007/084887 dated Oct. 9, 2008 (6 pages).

* cited by examiner

*Primary Examiner* — James D Anderson
*Assistant Examiner* — Gregg Polansky
(74) *Attorney, Agent, or Firm* — Foleyn & Lardner, LLP

(57) ABSTRACT

Unit doses of factor Xa inhibitor compounds and methods of using these compounds for inhibiting blood coagulation in a human patient are taught herein. The unit dose of the factor Xa inhibitor compounds disclosed herein required to inhibit coagulation in a primate is lower than the unit dose required to obtain similar levels of coagulation inhibition in other animal models, such as rodents. Also taught are in vitro assays useful in predicting in vivo antithrombotic activity in humans.

5 Claims, 6 Drawing Sheets

UNIT DOSE FORMULATIONS AND METHODS OF TREATING THROMBOSIS WITH AN ORAL FACTOR XA INHIBITOR

CROSS REFERENCE TO RELATED APPLICATIONS

This application claims the benefit under 35 U.S.C. §119(e) of U.S. Provisional Patent Application Nos. 60/873,792 filed on Dec. 8, 2006 and 60/947,629 filed on Jul. 2, 2007, both of which are hereby incorporated by reference in their entirety.

BACKGROUND OF THE INVENTION

1. Field of the Invention

This invention is directed to methods of inhibiting coagulation using a particular dose of a factor Xa inhibitor. The invention is also directed to an assay that measures thrombin generation in blood to assess the antithrombotic activity of a test compound.

2. State of the Art

Hemostasis, the control of bleeding, occurs by surgical means, or by the physiological properties of vasoconstriction and coagulation. Although platelets and blood coagulation are both involved in restoring hemostasis and in thrombotic diseases, certain components of the coagulation cascade are primarily responsible for the amplification and acceleration of the processes involved in platelet aggregation and fibrin deposition which are major events in thrombosis and hemostasis.

Clot formation involves the conversion of fibrinogen to fibrin which polymerizes into a network to restore hemostasis after injury. A similar process results in occluded blood vessels in thrombotic diseases. The conversion of fibrinogen to fibrin is catalyzed by thrombin, the end product of a series of reactions in the blood coagulation cascade. Thrombin is also a key player in activating platelets, thereby contributing to thrombosis under conditions of both arterial and venous blood flow. For these reasons, it has been postulated that efficient regulation of thrombin can lead to efficient regulation of thrombosis. Several classes of currently used anticoagulants directly or indirectly affect thrombin (i.e. unfractionated heparins, low-molecular weight heparins, heparin-like compounds, pentasaccharide and warfarin). Direct or indirect inhibition of thrombin activity has also been the focus of a variety of anticoagulants in clinical development (reviewed by Eriksson and Quinlan, *Drugs* 11: 1411-1429, 2006).

Prothrombin, the precursor for thrombin, is converted to the active enzyme by factor Xa (fXa). Localized activation of tissue factor/factor VIIa mediated factor Xa generation is amplified by the factor IXa/factor VIIIa complex and leads to prothrombinase assembly on activated platelets. Factor Xa, as a part of the prothrombinase complex, is the sole enzyme responsible for sustained thrombin formation in the vasculature. Factor Xa is a serine protease, the activated form of its precursor Factor X, and a member of the calcium ion binding, gamma carboxyglutamic acid (GLA)-containing, vitamin K dependent, and blood coagulation factors. Unlike thrombin, which acts on a variety of protein substrates including fibrinogen and the PAR receptors (Protease activated receptors, Coughlin, *J. Thrombosis Haemostasis* 3: 1800-1814, 2005), factor Xa appears to have a single physiologic substrate, namely prothrombin. Since one molecule of factor Xa may be able to generate greater than 1000 molecules of thrombin (Mann, et al., *J. Thrombosis. Haemostasis* 1: 1504-1514, 2003), direct inhibition of factor Xa as a way of indirectly inhibiting the formation of thrombin may be an efficient anticoagulant strategy. This assertion is based on the key role of prothrombinase in thrombin synthesis and on the fact that inhibition of prothrombinase will have a pronounced effect on the overall platelet aggregation and clotting pathways.

Activated proteases such as factor VIIa, factor IXa or factor Xa have poor proteolytic activity on their own. However, their assembly into cofactor-dependent, membrane-bound complexes significantly enhances their catalytic efficiencies. This effect is most dramatic for factor Xa, where the efficiency is increased by a factor of $10^5$ (Mann, et al., *Blood* 76(1): 1-16, 1990). Due to the higher concentration of the zymogens present in blood (1.4 µM prothrombin versus 150 nM factor Xa) and the kinetics of activation, a smaller amount of factor Xa than thrombin needs to be inhibited to achieve an anticoagulant effect. Indirect proof of the hypothesis of superiority of factor Xa as a therapeutic target compared to thrombin can also be found in clinical trials for the prevention of deep vein thrombosis. Fondaparinux, an antithrombin III dependent factor Xa inhibitor, was proven to be superior to enoxaparin (a low molecular weight heparin that inhibits both thrombin and factor Xa) in four trials of orthopedic surgery (Turpie, et al., *Archives Internal Medicine* 162(16): 1833-1840, 2002). Therefore, it has been suggested that compounds which selectively inhibit factor Xa may be useful as in vitro diagnostic agents, or for therapeutic administration in certain thrombotic disorders, see e.g., WO 94/13693.

SUMMARY OF THE INVENTION

Comparative modeling of the extent of changes in prothrombinase activity to levels of antithrombotic efficacy has lead to the discovery of the therapeutic activity in humans of factor Xa inhibitors. This invention is directed to a method of inhibiting coagulation in a human patient using a coagulation inhibiting amount of a factor Xa inhibitor. Specifically, orally available, direct inhibitors of factor Xa are effective to inhibit coagulation in a human patient when administered to the patient in an aggregate daily amount of between about 0.01 and about 2.0 milligrams per kilogram based on the total weight of the patient ("mg/kg"). It is contemplated that this dose will be effective for any compound which specifically inhibits factor Xa and particularly effective for factor Xa inhibitors of Formula I, II, III, IV, or V described below.

The invention is also directed to a method of assessing the coagulation status of the patient. It is contemplated that this method of assessing the coagulation status may be used to test a number of different classes of anticoagulants in addition to factor Xa inhibitors.

In one aspect of the invention, the method comprises administering to the patient a coagulation inhibiting amount of a compound of Formula I:

A-Q-D-E-G-J-X     I wherein:

A is selected from:
 (a) $C_1$-$C_6$-alkyl;
 (b) $C_3$-$C_8$-cycloalkyl;
 (c) —N($R^1$,$R^2$), N($R^1$,$R^2$)—C(=N$R^3$)—, N($R^1$,$R^2$)—C(=N$R^3$)—N($R^4$)—, $R^1$—C(=N$R^3$)—, $R^1$—C(=N$R^3$)—N($R^4$)—;
 (d) phenyl, which is independently substituted with 0-2 R substituents;
 (e) naphthyl, which is independently substituted with 0-2 R substituents; and a monocyclic or fused bicyclic heterocyclic ring system having from 5 to 10 ring atoms, wherein 1-4 ring atoms of the ring system are selected from N, O and S, and wherein the ring system may be substituted with 0-2 R substituents;

R is selected from:
H, halo, —CN, —CO$_2$R$^1$, —C(=O)—N(R$^1$,R$^2$), —(CH$_2$)$_m$—CO$_2$R$^1$, —(CH$_2$)$_m$—C(=O)—N(R$^1$,R$^2$), —NO$_2$, —SO$_2$N(R$^1$R$^2$), —SO$_2$R$^1$, —(CH$_2$)$_m$—NR$^1$R$^2$, —(CH$_2$)$_m$—C(=NR$^3$)—R$^1$, —(CH$_2$)$_m$—C(=NR$^3$)—N(R$^1$,R$^2$), —(CH$_2$)$_m$—N(R$^4$)—C(=NR$^3$)—N(R$^1$,R$^2$), —(CH$_2$)$_m$NR$^1$-group appended to a 3 to 6 membered heterocyclic ring containing from 1-4 heteroatoms selected from N, O and S, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CF$_3$, —OR$^2$, and a 5-6 membered heterocyclic system containing from 1-4 heteroatoms selected from N, O and S, wherein from 1-4 hydrogen atoms on the heterocyclic system may be independently replaced with a member selected from the group consisting of halo, —C$_1$-C$_4$-alkyl, —C$_{1-4}$alkyl-CN, —C$_{2-6}$alkenyl, —C$_{2-6}$alkynyl, —C$_{3-8}$cycloalkyl, —C$_{0-4}$alkylene-C$_{3-8}$cycloalkyl and —NO$_2$;

m is an integer of 0-2;

R$^1$, R$^2$, R$^3$ and R$^4$ are independently selected from the group consisting of:
H, —OR$^5$, —N(—R$^5$,—R$^6$), —C$_{1-4}$alkyl, —C$_{2-6}$alkenyl, —C$_{2-6}$alkynyl, —C$_{3-8}$cycloalkyl, —C$_{0-4}$alkylene-C$_{3-8}$cycloalkyl, —C$_{0-4}$alkylphenyl and —C$_{0-4}$alkylnaphthyl, wherein from 1-4 hydrogen atoms on the ring atoms of the phenyl and naphthyl moieties may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkylene-C$_{3-8}$cycloalkyl, —CN, and —NO$_2$; or R$^1$ and R$^2$, or R$^2$ and R$^3$ taken together can form a 3-8 membered cycloalkyl or a heterocyclic ring system, wherein the heterocyclic ring system may have from 3 to 10 ring atoms, with 1 to 2 rings being in the ring system and contain from 1-4 heteroatoms selected from N, O and S, wherein from 1-4 hydrogen atoms on the heterocyclic ring system may be independently replaced with a member selected from the group consisting of halo, C$_1$-C$_4$-alkyl, —CN, —C$_{2-6}$alkenyl, —C$_{2-6}$alkynyl, —C$_{3-8}$cycloalkyl, —C$_{0-4}$alkylene-C$_{3-8}$cycloalkyl and —NO$_2$;

R$^5$ and R$^6$ are independently selected from the group consisting of:
H, —C$_{1-4}$alkyl, —C$_{2-6}$alkenyl, —C$_{2-6}$alkynyl, —C$_{3-8}$cycloalkyl, —C$_{0-4}$alkylene-C$_{3-8}$cycloalkyl, —C$_{0-4}$alkylphenyl and —C$_{0-4}$alkylnaphthyl, wherein from 1-4 hydrogen atoms on the ring atoms of the phenyl and naphthyl moieties may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkylene-C$_{3-8}$cycloalkyl, —CN, and —NO$_2$; or R$^5$ and R$^6$ taken together can form a 3-8 membered cycloalkyl or a heterocyclic ring system, wherein the heterocyclic ring system may have from 3 to 10 ring atoms, with 1 to 2 rings being in the ring system and contain from 1-4 heteroatoms selected from N, O and S, wherein from 1-4 hydrogen atoms on the heterocyclic ring system may be independently replaced with a member selected from the group consisting of halo, —C$_1$-C$_4$-alkyl, —CN, —C$_{2-6}$alkenyl, —C$_{2-6}$alkynyl, —C$_{3-8}$cycloalkyl, —C$_{0-4}$alkylene-C$_{3-8}$cycloalkyl and —NO$_2$;

Q is a member selected from the group consisting of:
a direct link, —CH$_2$—, —C(=O)—, —O—, —N(R$^7$)—, —N(R$^7$)CH$_2$—, —CH$_2$N(R$^7$)—, —C(=NR$^7$)—, —C(=O)—N(R$^7$)—, —N(R$^7$)—C(=O)—, —S—, —SO—, —SO$_2$—, —SO$_2$—N(R$^7$)— and —N(R$^7$)—SO$_2$—;

R$^7$ is selected from:
H, —C$_{1-4}$alkyl, —C$_{2-6}$alkenyl, —C$_{2-6}$alkynyl, —C$_{3-8}$cycloalkyl, —C$_{0-4}$alkylene-C$_{3-8}$cycloalkyl, —C$_{0-4}$alkylenephenyl and —C$_{0-4}$alkylenenaphthyl, wherein from 1-4 hydrogen atoms on the ring atoms of the phenyl and naphthyl moieties may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkylene-C$_{3-8}$cycloalkyl, —CN, and —NO$_2$;

D is a direct link or is a member selected from the group consisting of:
(a) phenyl, which is independently substituted with 0-2 R$^{1a}$ substituents;
(b) naphthyl, which is independently substituted with 0-2 R$^{1a}$ substituents; and
(c) a monocyclic or fused bicyclic heterocyclic ring system having from 5 to 10 ring atoms, wherein 1-4 ring atoms of the ring system are selected from N, O and S, and wherein the ring system may be substituted from 0-2 R$^{1a}$ substituents;

R$^{1a}$ is selected from:
halo, —C$_{1-4}$alkyl, —C$_{2-6}$alkenyl, —C$_{2-6}$alkynyl, —C$_{3-8}$cycloalkyl, —C$_{0-4}$alkylene-C$_{3-8}$cycloalkyl, —CN, —NO$_2$, —(CH$_2$)$_n$NR$^{2a}$R$^{3a}$, —(CH$_2$)CO$_2$R$^{2a}$, —(CH$_2$)$_n$CONR$^{2a}$R$^{3a}$, —SO$_2$NR$^{2a}$R$^{3a}$, —SO$_2$R$^{2a}$, —CF$_3$, —OR$^{2a}$, and a 5-6 membered aromatic heterocyclic system containing from 1-4 heteroatoms selected from N, O and S, wherein from 1-4 hydrogen atoms on the aromatic heterocyclic system may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkylene-C$_{3-8}$cycloalkyl, —CN and —NO$_2$;

R$^{2a}$ and R$^{3a}$ are independently selected from the group consisting of:
H, —C$_{1-4}$alkyl, —C$_{2-6}$alkenyl, —C$_{2-6}$alkynyl, —C$_{3-8}$cycloalkyl, —C$_{0-4}$alkylene-C$_{3-8}$cycloalkyl, —C$_{0-4}$alkylene-phenyl and —C$_{0-4}$alkylene-naphthyl, wherein from 1-4 hydrogen atoms on the ring atoms of the phenyl and naphthyl moieties may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkylene-C$_{3-8}$cycloalkyl, —CN and —NO$_2$;

n is an integer of 0-2;

E is a direct link or a member selected from the group consisting of:
—C$_{1-2}$-alkylene-, —O—, —S—, —SO—, —SO$_2$—, —C$_{0-1}$-alkylene-C(=O), —C$_{0-1}$-alkylene-C(=O)—N(—R$^8$)—C$_{0-1}$-alkylene-, —C$_{0-1}$-alkylene-N(—R$^8$)—C(=O)—C$_{0-1}$-alkylene-, —N(—R$^8$)—C(=O)—N(—R$^8$)— and —C$_{0-1}$-alkylene-N(—R$^8$)—;

R$^8$ is a member selected from the group consisting of:
H; —C$_{1-4}$-alkyl; —C$_{0-4}$-alkylenearyl; —C$_{0-4}$-alkyleneheteroaryl; —C$_{1-4}$-alkylene-C(=O)—OH, —C$_{1-4}$-alkylene-C(=O)—O—C$_{1-4}$-alkyl, and —C$_{1-4}$-alkylene-C(=O)—N(—R$^{2b}$, —R$^{3b}$);

R$^{2b}$ and R$^{3b}$ are each a member independently selected from the group consisting of:
H, —C$_{1-4}$-alkyl; —C$_{0-4}$-alkylene-aryl; —C$_{0-4}$-alkylene-heterocyclic group, and R$^{2b}$ and R$^{3b}$ together with the N atom to which they are attached can form a 5-8 membered heterocyclic ring containing 1-4 heteroatoms selected from N, O and S, wherein the heterocyclic ring may be substituted with 0-2 $R^{1c}$ groups;

$R^{1c}$ is a member selected from the group consisting of:
halo; —$C_{1-4}$-alkyl; —CN; —NO$_2$; —C(=O)—N(—$R^{2c}$, —$R^{3c}$); —C(=O)—O$R^{2c}$; —(CH$_2$)$_q$—N(—$R^{2c}$, —$R^{3c}$); —SO$_2$—N(—$R^{2c}$, —$R^{3c}$); —SO$_2$$R^{2c}$; —CF$_3$; and —(CH$_2$)$_q$—O$R^{2c}$;

$R^{2c}$ and $R^{3c}$ are each independently a member selected from the group consisting of:
H; —$C_{1-4}$-alkyl; and —$C_{1-4}$-alkylene-aryl;

q is an integer of 0-2;

G is a member selected from the group consisting of:
(a) $C_2$-alkenyl or $C_{3-8}$-cycloalkenyl, wherein the alkenyl and cycloalkenyl attachment points are the alkenyl carbon atoms and wherein the —$C_2$-alkenyl or —$C_{3-8}$-cycloalkenyl are substituted with 0-4 $R^{1d}$ groups;
(b) a phenyl group wherein the ring carbon atoms of the phenylene group are substituted with 0-4 $R^{1d}$ groups;
(c) a 3-8 membered heterocyclic ring system containing 1-4 heteroatoms selected from N, O and S, wherein 0-2 ring atoms of the heterocyclic ring may be substituted with 0-4 $R^{1d}$ groups; and,
(d) an 8-10 membered fused heterocyclic bicyclic ring system, containing 1-4 heteroatoms selected from N, O and S, wherein 0-2 ring atoms of the fused bicyclic ring system may be substituted with 0-4 $R^{1d}$ groups;

$R^{1d}$ is a member selected from the group consisting of:
H, halo; $C_{1-6}$-alkyl, aryl, —CN; —NO$_2$; —(CH$_2$)$_{0-6}$—N$R^{2d}R^{3d}$; —SO$_2$N$R^{2d}R^{3d}$; —SO$_2$$R^{2d}$; —CF$_3$; —(CH$_2$)$_{0-6}$—O$R^{2d}$; —O—(CH$_2$)$_{1-6}$O$R^{2d}$; —O—(CH$_2$)$_{1-6}$—C(=O)—O—$R^{2d}$; —O—(CH$_2$)$_{1-6}$—C(=O)—N($R^{2d}$,$R^{3d}$); —N($R^{5a}$)—(CH$_2$)$_{1-6}$—O$R^{2d}$; —N($R^{5a}$)—(CH$_2$)$_{1-6}$—N($R^{2d}$,$R^{3d}$); —C(=O)—N($R^{2d}$,$R^{3d}$); —N($R^{5a}$)—(CH$_2$)$_{1-6}$—C(=O)—N($R^{2d}$, $R^{3d}$); —N(—(CH$_2$)$_{1-6}$—O$R^{2d}$)$_2$; —N($R^{5a}$)—(CH$_2$)$_{1-6}$—O$R^{2d}$; —N($R^{5a}$)—C(=O)—$R^{2d}$; —N($R^{5a}$)—SO$_2$—$R^{2d}$; —(CH$_2$)$_{0-6}$—C(=O)—O—$R^{2d}$; —(CH$_2$)$_{0-6}$—C(=O)—N($R^{2d}$,$R^{3d}$); —(CH$_2$)$_{0-6}$—C(=N$R^{2d}$)—N($R^{3d}$,$R^{4d}$); —(CH$_2$)$_{0-6}$—N($R^{5a}$)C(=N$R^{2d}$)—N($R^{3d}$,$R^{4d}$); a —(CH$_2$)$_{0-6}$—N($R^{3d}$)$C_{5-6}$ membered heterocyclic ring containing 1-4 heteroatoms selected from N, O and S, and a —(CH$_2$)$_{0-6}$-5-6 membered heterocyclic ring containing 1-4 heteroatoms selected from N, O and S;

$R^{5a}$,$R^{2d}$,$R^{3d}$ and $R^{4d}$ are each independently a member selected from the group consisting of:
H; $C_{1-6}$-alkyl; $C_{1-6}$-alkylaryl; —CN; —NO$_2$; carbocyclic aryl; —CN; —NO$_2$; or $R^{2d}$ and $R^{3d}$ taken together with the N atoms they are independently attached form a 5-7 membered heterocyclic ring; or $R^{3d}$ and $R^{4d}$ taken together with the N atom to which they are attached form a 5-8 membered heterocyclic ring containing 1-4 heteroatoms selected from N, O and S;

J is a direct link or is a member selected from the group consisting of:
—N(—$R^9$)—C(=O)—; —C(=O)—N(—$R^9$)—; —O—; —S—; —SO—; —SO$_2$—; —CH$_2$—; —N(—$R^9$)—; and —N(—$R^9$)—SO$_2$—;

$R^9$ is a member selected from the group consisting of:
H; —$C_{1-4}$-alkyl; —$C_{0-4}$-alkyl-carbocyclic aryl; —(CH$_2$)$_{0-4}$-5-6 membered heterocyclic ring containing 1-4 heteroatoms selected from N, O and S; —(CH$_2$)$_{1-6}$—C(=O)—O—$C_{1-4}$-alkyl; and —(CH$_2$)$_{1-6}$—C(=O)—N($R^{6a}$,$R^{6b}$);

$R^{6a}$ and $R^{6b}$ are each a member independently selected from the group consisting of:
H and —$C_{1-6}$-alkyl;

X is a member selected from the group consisting of:
(a) phenyl substituted with 0-3 $R^{1e}$ groups;
(b) naphthyl substituted with 0-3 $R^{1e}$ groups and
(c) a 6-membered aromatic heterocyclic ring system containing 1-3 N atoms and having 0-3 ring atoms substituted with 0-3 $R^{1e}$ groups; and
(d) an 8-10 membered fused aromatic heterocyclic bicyclic ring system containing 1-4 heteroatoms selected from N, O and S and 0-3 ring atoms of the fused heterocyclic bicyclic ring system are substituted with 0-3 $R^{1e}$ groups;

$R^{1e}$ is a member independently selected from the group consisting of:
Halo; CF$_3$; —$C_{1-4}$-alkyl; carbocyclic aryl; —$C_{0-2}$-alkylene-CN; —O—$R^{2e}$; —$C_{0-2}$-alkylene-C(=O)—O—$R^{2e}$; —$C_{0-2}$-alkylene-C(=O)—N($R^{2e}$,$R^{3e}$); —$C_{0-2}$-alkylene-NO$_2$; —$C_{0-2}$-alkylene-N($R^{2e}$,$R^{3e}$); —$C_{0-2}$-alkylene-SO$_2$—N($R^{2e}$,$R^{3e}$); —$C_{0-2}$-alkylene-SO$_2$—$R^{2e}$; trihaloalkyl; —O—$C_{0-2}$-alkylene-O—$R^{2e}$; —$C_{0-2}$-alkylene-O—$R^{2e}$; —O—$C_{1-4}$-alkylene-C(=O)—N($R^{2e}$,$R^{3e}$); —$C_{1-4}$-alkylene-C(=O)—O—$R^{2e}$; —$C_{0-2}$-alkylene-N($R^{2e}$)—C(=O)—$R^{3e}$; —$C_{0-2}$-alkylene-N(—$R^{2e}$)—SO$_2$—$R^{3e}$; —CH$_2$—N($R^{2e}$)—C(=O)—$R^{3e}$; —CH$_2$—N($R^{2e}$)—SO$_2$—$R^{3e}$; —(CH$_2$)$_{0-6}$—N$R^{2e}R^{3e}$; —C(=O)—N($R^{2e}$,$R^{3e}$); —N(—(CH$_2$)$_{1-6}$—O$R^{2e}$)$_2$; —N($R^{10}$)—(CH$_2$)$_{1-6}$—O$R^{2e}$; —N($R^{10}$)—C(=O)—$R^{2e}$; —N($R^{10}$)—SO$_2$—$R^{2e}$; —C(=N($R^{10}$))—N($R^{2e}$,$R^{3e}$); and a —(CH$_2$)$_{0-6}$-5-6 membered heterocyclic ring containing 1-4 heteroatoms selected from N, O and S;

$R^{10}$, $R^{2e}$ and $R^{3e}$ are each independently a member selected from the group consisting of:
H; —$C_{1-4}$-alkyl; —$C_{0-2}$-alkylene-O—$R^{1g}$; —$C_{0-2}$-alkylene-N(—$R^{1g}$, —$R^{2g}$); —$C_{1-4}$-alkylene-carbocyclic aryl; —$C_{1-4}$-alkylene-heterocyclic; and $R^{10}$ and $R^{2e}$, or $R^{2e}$ and $R^{3e}$ together with the N atom to which they are attached can form 5-8 membered heterocyclic ring containing 1-4 heteroatoms selected from N, O and S which can be substituted with 0-2 $R^{1g}$ groups;

$R^{1g}$ and $R^{2g}$ are independently a member selected from the group of:
H; halo; —$C_{1-4}$-alkyl, a carbocyclic aryl group; a heterocyclic group; —CN; —C(=O)—N($R^{3g}$)$R^{4g}$; —C(=O)—O$R^{3g}$; —NO$_2$; —(CH$_2$)$_p$—N$R^{3g}R^{4g}$; —SO$_2$N$R^{3g}R^{4g}$; —SO$_2$$R^{3g}$; —CF$_3$; and —(CH$_2$)$_p$O$R^{3g}$;

p is an integer of 0-2; and $R^{3g}$ and $R^{4g}$ are each independently selected from the group consisting of:
H; $C_{1-4}$-alkyl and —$C_{0-4}$-alkylene-carbocyclic aryl;

or a pharmaceutically acceptable salt thereof.

In one embodiment, the coagulation inhibiting amount of the factor Xa inhibitor compound is an aggregate daily dose from between about 0.01 and about 2.0 mg/kg. In another embodiment, the coagulation inhibiting amount of the factor Xa inhibitor compound is an aggregate daily dose from between 0.1 and 1.5 mg/kg. In yet another embodiment, the amount is between about 0.4 and about 1.2 mg/kg.

In one embodiment, the coagulation inhibiting amount is administered to the patient once a day. In another embodiment, the coagulation inhibiting amount is administer to the patient in one day but dosed several times a day, i.e., twice ("BID") or three times a day ("TID").

In one embodiment, the pharmaceutically acceptable salt of the factor Xa inhibitor compound is a maleate salt. In another embodiment, the compound of formula I is the compound of formula II:

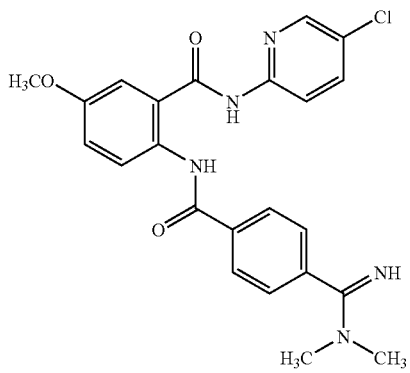

or pharmaceutically acceptable salt thereof. In some embodiments, the salt is a maleate salt. In one embodiment, the coagulation inhibiting amount is an aggregate daily dose of a compound of formula II or salt thereof from between about 0.01 and about 2.0 mg/kg or between about 0.1 and about 1.5 mg/kg or between about 0.4 and about 1.2 mg/kg.

In another embodiment, the factor Xa inhibitor compound is the maleate salt having the structure of formula III:

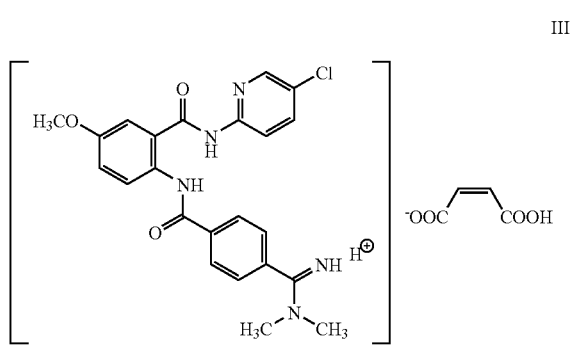

This invention is also directed to a unit dose formulation. This unit does is a pharmaceutical composition comprising a pharmaceutically acceptable carrier and a coagulation inhibiting amount of the factor Xa inhibitor compound of Formula I, II, IV, or V (as described below) or a pharmaceutically acceptable salt thereof, or the salt of Formula III. In some embodiments, the coagulation inhibiting amount is an aggregate daily does of between about 0.01 and about 2.0 mg/kg. In other embodiments, the dose is between about 0.1 and about 1.5 mg/kg or between about 0.4 and about 1.2 mg/kg.

The invention is also directed to an in vitro assay to determine the in vivo antithrombotic properties of a compound. The assay comprises the following steps:
 a) introducing a test compound into an in vitro sample of whole blood or plasma comprising tissue factor (TF) and a detectably-labeled thrombin substrate to form a test sample;
 b) determining the level of thrombin activity in the test sample by monitoring the cleavage of the detectably-labeled thrombin substrate in the test sample as a function of time;
 c) determining the level of thrombin activity in a control sample by monitoring the cleavage of the detectably-labeled thrombin substrate in the control sample as a function of time, wherein the control sample comprises whole blood or plasma comprising tissue factor (TF) and a detectably-labeled thrombin substrate;
 d) comparing the level of thrombin activity in the test sample and the control sample, wherein a lower level of thrombin activity in the test sample is an indication that the test compound has in vivo antithrombotic activity.

The blood and plasma may be anticoagulated or nonanticoagulated.

In certain embodiments of the invention, the detectably-labeled thrombin substrate is a Z-Gly-Gly-Arg-AMC.

DETAILED DESCRIPTION OF THE INVENTION

Figure 1A:
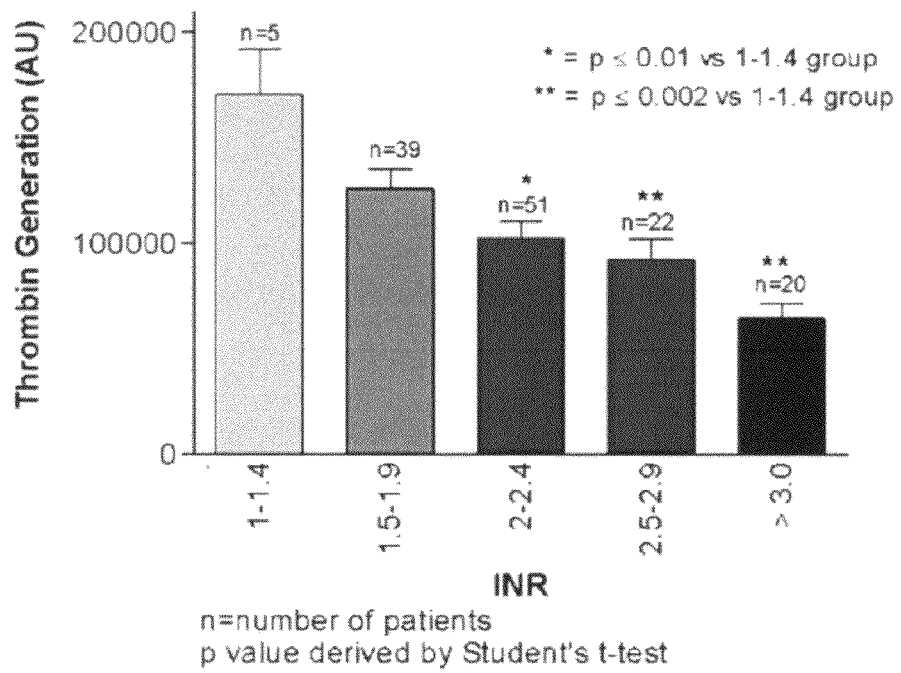
FIG. 1A shows the correlation of thrombin generation with the international normalized ratio (INR) in anticoagulated patients treated with warfarin. Thrombin generation was measured at 10 minutes in plasma samples from patients receiving stable warfarin therapy (n=137). Data from patients receiving warfarin therapy is presented as quintiles of the INR results. Error bars show standard errors.

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3$^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3$^{rd}$ edition (Cold Spring Harbor Laboratory Press (2002)).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

1. DEFINITIONS

In accordance with the present invention and as used herein, the following terms are defined with the following meanings, unless explicitly stated otherwise.

As used in the specification and claims, the singular form "a", "an" and "the" include plural references unless the context clearly dictates otherwise. For example, the term "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "aggregate daily dose" refers to the amount of drug or compound administered in a 24 hour period.

The term "test sample" or "assay solution" comprises whole blood or blood plasma (either anticoagulated or nonanticoagulated), tissue factor ("TF"), a detectably-labeled thrombin substrate, and a test compound. The solution may also contain a number of suitable solvents, such as dimethylsulfoxide (DMSO). In one embodiment, the blood or plasma in the test sample or assay solution is not treated or titrated with enzymes, including reptile venom enzymes, such as Reptilase®. In another embodiment, the blood or plasma is not platelet-rich.

The term "tissue factor" or TF is present in subendothelial tissue, platelets, and leukocytes and is necessary for the initiation of thrombin formation from the zymogen prothrombin. TF is also referred to as thromboplastin, factor III, or CD142. The TF used in the methods of this invention are preferably human recombinant human TF which is commercially available from Dade Behring Pharmaceuticals or American Diagnostica, Inc. The TF used in the assays may also be endogenous or a combination of endogenous and exogenous.

The term "test compound" as used herein refers to a non-peptidic compound having a molecular weight of less than 1500 Daltons. This term also refers to small heparinoid and saccharide moieties having of molecular weight of less than 5000 Daltons.

The term "control sample" refers to the test sample or assay solution where the test compound is absent.

The term "nonanticoagulated whole blood" refers to blood collected from a patient which has not received anticoagulation therapy by an antithrombotic agent. This also refers to blood from a patient that may have received anticoagulation therapy but any benefit or effect is no longer realized.

The term "anticoagulated whole blood" or "anticoagulated plasma" refers to blood or plasma taken from patients who recently underwent or are currently undergoing anticoagulant therapy. This also refers to blood from human donors which is obtained by venipuncture and collected in a medium containing exogenously added anticoagulant such as citrate, EDTA, or heparin.

The term "detectably-labeled thrombin substrate" refers to a thrombin substrate that is labeled by any number of well-known detectable labels. These labels include, but are not limited to, fluorescent labels, phosphorescent labels, chemiluminescent labels, electrochemiluminescent labels, and radioactive labels. In one embodiment of the invention, the labeled substrate is Z-Gly-Gly-Arg-AMC, commercially available from Bachem.

The term "antithrombotic activity" refers to the compounds ability to inhibit thrombus formation with acceptable effects on classical measures of coagulation parameters, platelets, and platelet function. Conditions characterized by undesired thrombosis include those involving the arterial and venous vasculature. With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

Evidence of antithrombotic activity will lend to usefulness in anticoagulant therapy for preventing coagulation of stored whole blood and to prevent coagulation in other biological samples for testing or storage.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 2-12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms. The term "alkylene" refers to an alkyl group which is divalent, i.e., —CH$_2$—.

As used herein, the terms "carbocyclic ring structure" and "$C_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy (—O—$C_{1-6}$ alkyl), loweralkyl (—$C_{1-6}$ alkyl), loweralkylamino (—NRR, where 1 or 2 of R is loweralkyl), hydroxy, halogen, cyano, hydroxyl, mercapto, nitro, thioalkoxy (—S-alkyl), carboxaldehyde (—OC(O)—H), carboxyl (—C(O)OH), carboalkoxy (—C(O)—O-alkyl) and carboxamide (—C(O)—NH$_2$), including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5-7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system," include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one heteroatom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement(s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocylic and bicyclic heterocyclic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4αH-carbazolyl, carbolinyl, chromanyl, chromenyl, cinnolinyl, decahydroquinolinyl, 2H,6H-1,5,2-dithiazinyl, dihydrofuro[2,3-β]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocylic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like, for example.

The term "methylene" refers to —$CH_2$—.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salts" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

2. METHODS OF INHIBITING BLOOD COAGULATION AND UNIT DOSE FORMULATIONS

One aspect of the invention provides methods of inhibiting blood coagulation in a human patient by administering to the patient a coagulation inhibiting amount of a factor Xa inhibitor compound. This aspect relates to the surprising discovery that the unit dose of the factor Xa inhibitor compounds disclosed herein required to inhibit coagulation in a primate is lower than the dose unit required to obtain similar levels of coagulation inhibition in other animal models, such as rodents. As described further in the Examples and Figures, this species specificity was demonstrated by in vivo assays and by in vitro extensions of prothrombin time (PT) in rat, rabbit, baboon and human plasma. A two-fold increase of PT was attained at concentrations of 8.9 µM in rat and 1.6 µM in rabbit as compared to the primates where the two-fold change in PT was observed at 1 µM in baboon and 0.4 µM in humans.

The factor Xa inhibitor compounds are useful in treating disease states in mammals which have disorders of coagulation such as in the treatment or prevention of unstable angina, refractory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries. Further, these compounds are useful for the treatment or prophylaxis of those diseases which involve the production and/or action of factor Xa/prothrombinase complex. This includes a number of thrombotic and prothrombotic states in which the coagulation cascade is activated which include but are not limited to, deep venous thrombosis, pulmonary embolism, myocardial infarction, stroke, thromboembolic complications of surgery and peripheral arterial occlusion. Other diseases treatable or preventable by the administration of compounds of this invention include, without limitation, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

Accordingly, one aspect of the invention provides for a method of inhibiting coagulation in a human patient in need thereof, comprising administering to the patient a coagulation inhibiting amount of a factor Xa inhibitor compound or pharmaceutically acceptable salt thereof, wherein the coagulation inhibiting amount of the factor Xa inhibitor compound is an aggregate daily dose from between 0.01 and 2.0 mg/kg. Specific embodiments of factor Xa inhibitor compounds are shown in Formula I, II, IV, V and salts thereof (such as Formula III) as set forth below. Further embodiments provide for methods of inhibiting coagulation in a human patient in need thereof, comprising administering to the patient a coagulation inhibiting amount of a factor Xa inhibitor compound, or pharmaceutically acceptable salt thereof, wherein the coagulation inhibiting amount of the factor Xa inhibitor compound is an aggregate daily dose from between 0.05 and 2.0 mg/kg; alternatively, the coagulation inhibiting amount of the factor Xa inhibitor compound is an aggregate daily dose from between 0.1 and 2.0 mg/kg; or alternatively, the coagulation inhibiting amount of the factor Xa inhibitor compound is an aggregate daily dose from between 0.1 or 0.2 and 1.5 mg/kg; or alternatively, the coagulation inhibiting amount of the factor Xa inhibitor compound is an aggregate daily dose from between 0.4 and 1.2 mg/kg; or alternatively, the coagulation inhibiting amount of the factor Xa inhibitor compound is an aggregate daily dose from between 0.43 and 1.15 mg/kg; or alternatively, the coagulation inhibiting amount of the factor Xa inhibitor compound is an aggregate daily dose from between 0.45 and 0.55 mg/kg. In still another embodiment of the invention, the amount of the factor Xa inhibitor compound administered to a human is such that the serum level is about 1 µM or less.

Another aspect of the invention provides for the unit dose formulations comprising a pharmaceutical composition comprising a pharmaceutically acceptable carrier and a coagulation inhibition amount of the factor Xa inhibitor compound, or pharmaceutically acceptable salt thereof, wherein the coagulation inhibiting amount of the factor Xa inhibitor compound is an aggregate daily dose between 0.01 to 2.0 mg/kg; alternatively, the coagulation inhibiting amount of the factor Xa inhibitor compound is an aggregate daily dose from between 0.05 and 2.0 mg/kg; alternatively, the coagulation inhibiting amount of the factor Xa inhibitor compound is an aggregate daily dose from between 0.1 and 2.0 mg/kg; or alternatively, the coagulation inhibiting amount of the factor Xa inhibitor compound is an aggregate daily dose from between 0.2 and 1.5 mg/kg; or alternatively, the coagulation inhibiting amount of the factor Xa inhibitor compound is an aggregate daily dose from between 0.4 and 1.2 mg/kg; or alternatively, the coagulation inhibiting amount of the factor Xa inhibitor compound is an aggregate daily dose from between 0.43 and 1.15 mg/kg; or alternatively, the coagulation inhibiting amount of the factor Xa inhibitor compound is an aggregate daily dose from between about 0.45 and about 0.55 mg/kg.

The formulations are further described in the section titled "formulations."

3. THROMBIN GENERATION ASSAY

Current measures for monitoring coagulation status (activated partial thromboplastin time (aPTT), prothrombin time (PT), international normalized ratio (INR), activated clotting time (ACT), anti fXa units) have been developed for existing anticoagulants (i.e., heparins and warfarin). The available tests are not sensitive enough to evaluate therapeutic concentrations of direct fXa inhibitors.

Since the true target of fXa inhibitors is the membrane associated prothrombinase complex, an assay measuring thrombin generation is a superior measure of the level of anticoagulation achieved in patients dosed with direct fXa inhibitors. Betrixaban, an orally bioavailable fXa inhibitor in advanced stages of clinical development (Phase II), was used to validate this hypothesis. Betrixaban is an active site directed, competitive inhibitor of human fXa (Ki=117 pM) and exhibits a greater than 86,000 fold specificity against related proteases such as thrombin, factor VIIa, factor IXa, activated protein C, tissue plasminogen activator, plasmin and trypsin. Betrixaban is a potent inhibitor of the prothrombinase complex (Ki=801 pM).

Assays known in the art, such as those described in Sinha et al., *ATVB* 2003, 23: 1098-1104, incorporated by reference in its entirety herein, are distinguishable from those described herein in that extra steps, such as treating the blood with snake venom, or materials are required or different measurements are being taken. For example, the assays described in Sinha et al. required that the blood plasma be treated with Reptilase® to remove fibrinogen or that platelet-rich plasma be used or that thrombin be measured indirectly with markers such as thrombin antithrombin III complexes.

An aspect of the invention provides in vitro assays that are predictive of whether a compound has in vivo antithrombotic activity. The antithrombotic activity can be determined using whole blood measuring the thrombin activity. The amount of thrombin is correlated with anticoagulation activity in FIGS. 1A, 1B, and 1C. This assay is further correlated with in vivo anticoagulation activity and discussed more thoroughly in FIG. 2 and the Examples.

The assays involve determining thrombin activity in the presence and absence of a test compound. In one embodiment, an assay solution is prepared. The assay solution is comprised of nonanticoagulated whole blood, tissue factor (TF), and a detectably-labeled thrombin substrate, such as Z-Gly-Gly-Arg AMC. A test compound of interest is added to the assay solution and the cleavage of the detectably-labeled thrombin substrate is measured as a function of time. The order of introduction of the components into the assay solution can be varied.

A control assay is also performed with the assay solution in the absence of a test compound. A reduction in thrombin activity, as indicated by a decrease in thrombin substrate cleavage, in the assay with the test compound relative to the control assay indicates that the test compound has antithrombotic activity in vivo.

In an alternative embodiment, the assay does not include exogenously added TF. Instead the assay solution is stirred to activate the TF endogenously present in the cells in whole blood.

In other embodiments of the assay, the assay solution is comprised of anticoagulated whole blood or anticoagulated plasma instead of nonanticoagulated whole blood.

Accordingly, one aspect of the invention provides for an in vitro assay to determine whether a compound has in vivo antithrombotic activity comprising:
  a) introducing a test compound into an in vitro sample of nonanticoagulated whole blood comprising tissue factor (TF) and a detectably-labeled thrombin substrate to form a test sample;
  b) determining the level of thrombin activity in the test sample by monitoring the cleavage of the detectably-labeled thrombin substrate in the test sample as a function of time;
  c) determining the level of thrombin activity in a control sample by monitoring the cleavage of the detectably-labeled thrombin substrate in the control sample as a function of time, wherein the control sample comprises nonanticoagulated whole blood comprising tissue factor (TF) and a detectably-labeled thrombin substrate;
  d) comparing the level of thrombin activity in the test sample and the control sample, wherein a lower level of thrombin activity in the test sample is an indication that the test compound has in vivo antithrombotic activity.

In other specific embodiments, the anticoagulated whole blood of a) is replaced with either nonanticoagulated whole blood, anticoagulated plasma, or nonanticoagulated plasma.

2. FACTOR Xa INHIBITOR COMPOUNDS

Several factor Xa inhibitors have been reported as polypeptides derived from hematophagous organisms, as well as compounds which are not large polypeptide-type inhibitors. Additional factor Xa inhibitors include small molecule organic compounds, such as nitrogen containing heterocyclic compounds which have amidino substituent groups, wherein two functional groups of the compounds can bind to factor Xa at two of its active sites. For example, WO 98/28269 describes pyrazole compounds having a terminal amidino (—C(=NH)—NH$_2$) group; WO 97/21437 describes benzimidazole compounds substituted by a basic radical which are connected to a naphthyl group via a straight or branched chain alkylene, —C(=O)— or —S(=O)$_2$— bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group. Additional reported factor Xa inhibitors include those having a structure comprising a phenyl-amidino, phenyl, and halo-phenyl connected via amide linkages (U.S. Pat. Nos. 6,376,515 and 6,844,367). Other factor Xa inhibitors have replaced the halo-phenyl with a halo-pyridyl (see U.S. Pat. Nos. 6,376,515 B2 and 6,835,739). In specific embodiments of this invention, the factor Xa inhibitors are compounds of the Formula I described above. Compounds of Formula I are disclosed in U.S. Pat. Nos. 6,844,367 and 6,376,515, incorporated by reference in its entirety herein.

In some embodiments of the invention, the factor Xa inhibitor is a compound of Formula IV:

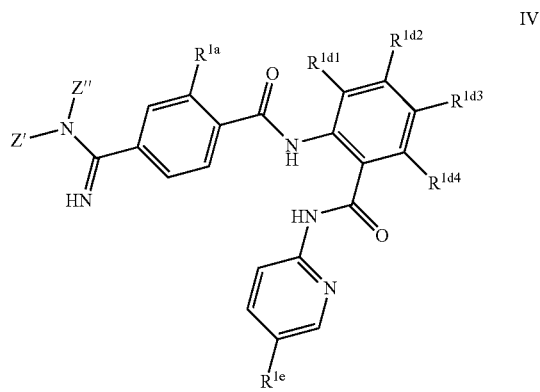

wherein:
Z' and Z" are each independently a $C_1$-$C_6$ alkyl which is optionally substituted with a hydroxyl, carboxylic acid or carboxylic acid ester group;

$R^{1a}$ is selected from the group consisting of:
H, —F, —Cl, and Br;

$R^{1d2}$ and $R^{1d4}$ are each H;

$R^{1d1}$ and $R^{1d3}$ are each independently a member selected from the group consisting of:
H, —Cl, —F, —Br, —OH and —OCH$_3$; and $R^{1e}$ is a member selected from the group consisting of:
—F, —Cl, —Br, —OH, —CH$_3$, and —OCH$_3$, or a pharmaceutically acceptable salt thereof.

Exemplary compounds of Formula IV are selected from the following:

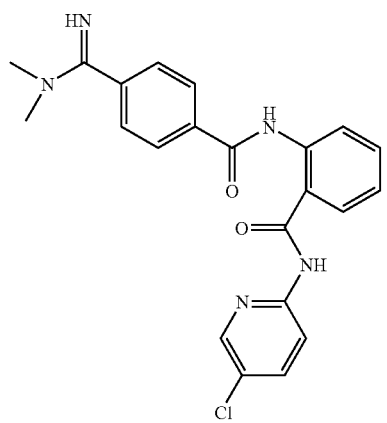

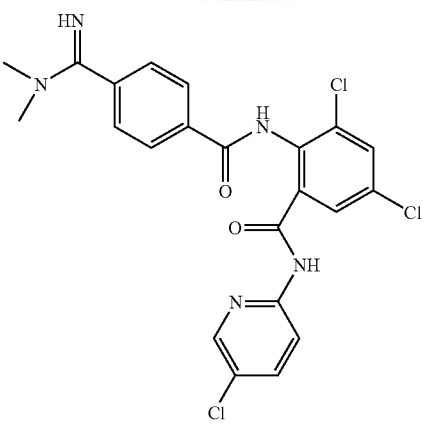

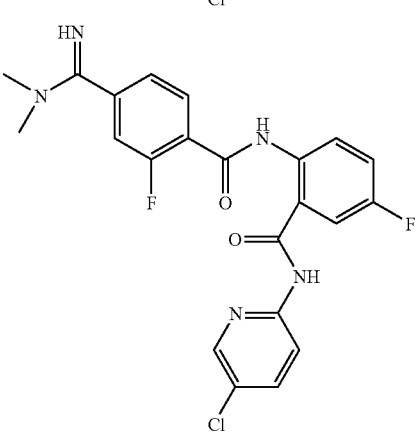

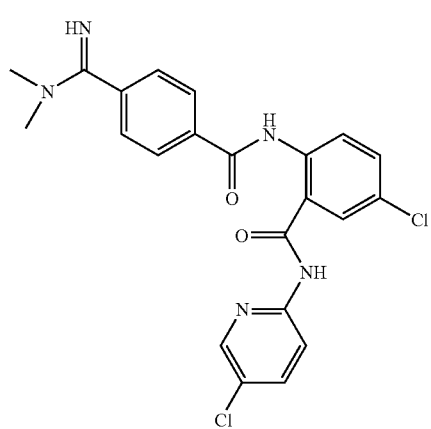

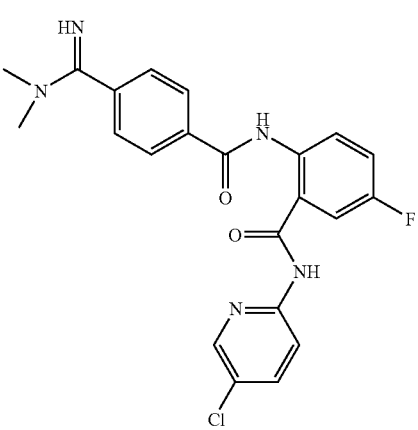

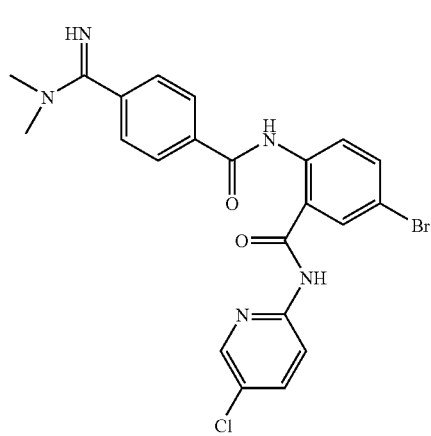

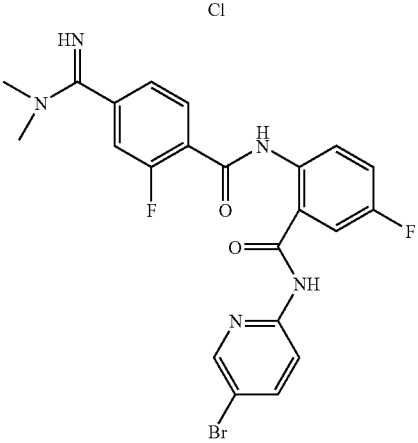

-continued
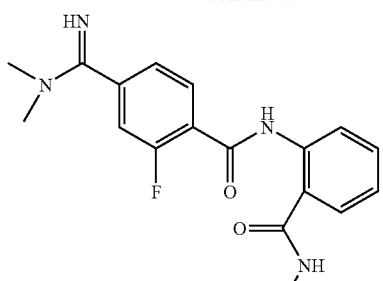
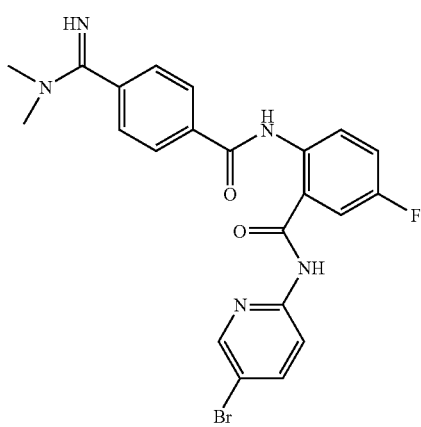
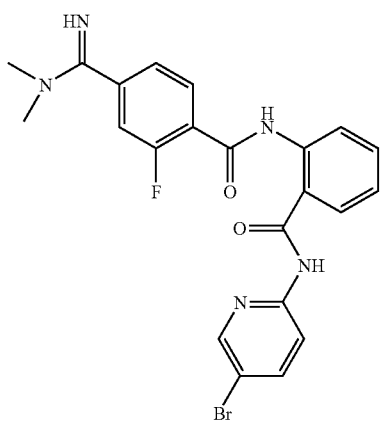
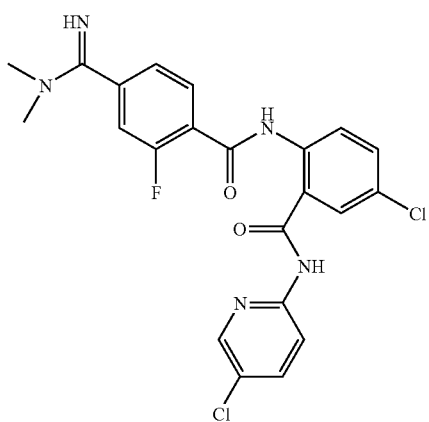
-continued
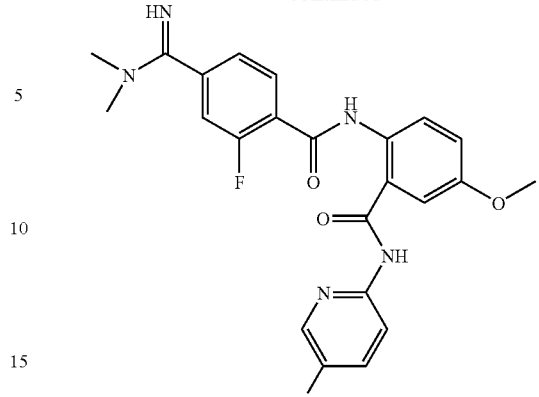
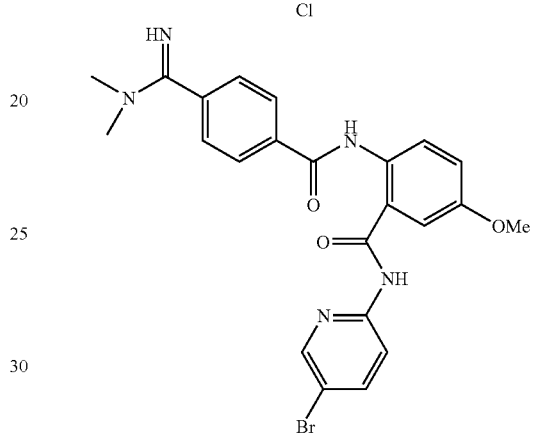
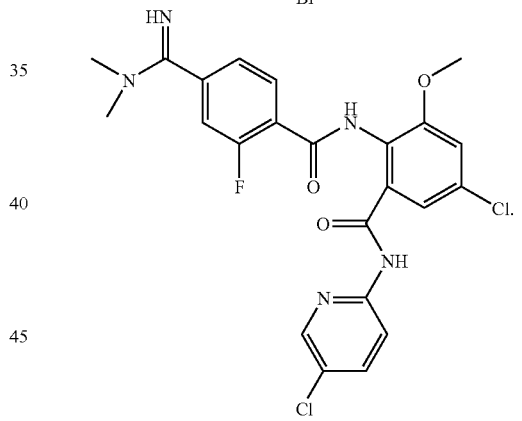
In another embodiment of the invention, the factor Xa inhibitor is a compound of formula V:
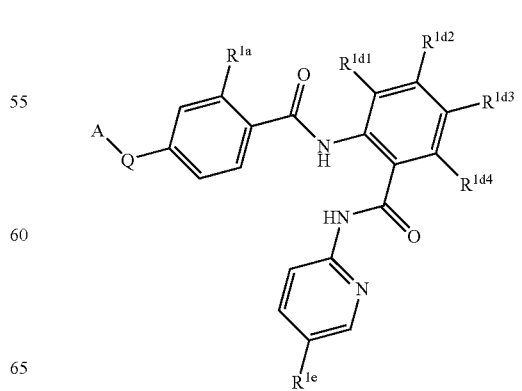

wherein:
A-Q is a member selected from the group consisting of:

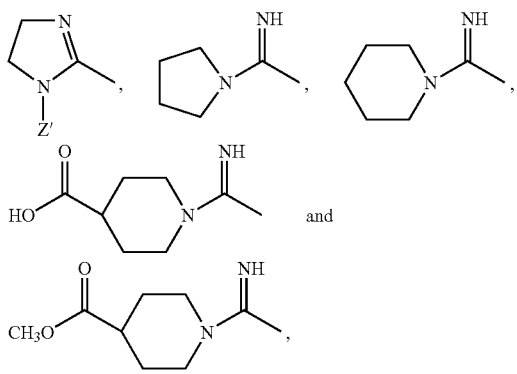

and

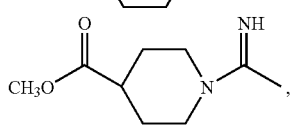

where Z' is a $C_{1-6}$ alkyl which is optionally substituted with a hydroxyl, carboxylic acid or carboxylic acid ester group;
$R^{1a}$ is selected from the group consisting of:
  H, —F, —Cl, and Br;
$R^{1d2}$ and $R^{1d4}$ are each H;
$R^{1d1}$ and $R^{1d3}$ are each independently a member selected from the group consisting of:
  H, —Cl, —F, —Br, —OH and —OCH$_3$;
$R^{1e}$ is a member selected from the group consisting of:
  —F, —Cl, —Br, —OH, —CH$_3$, and —OCH$_3$,
or a pharmaceutically acceptable salt thereof.

Exemplary compounds of Formula V include, but are not limited to:

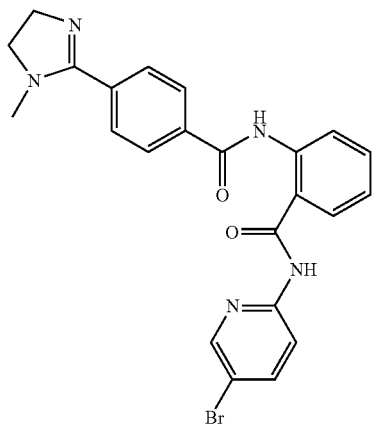

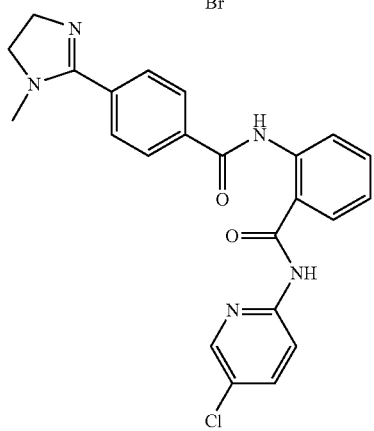

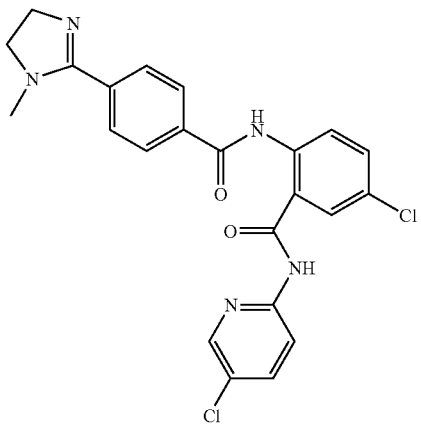

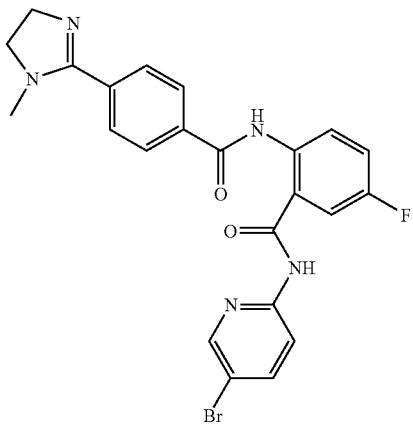

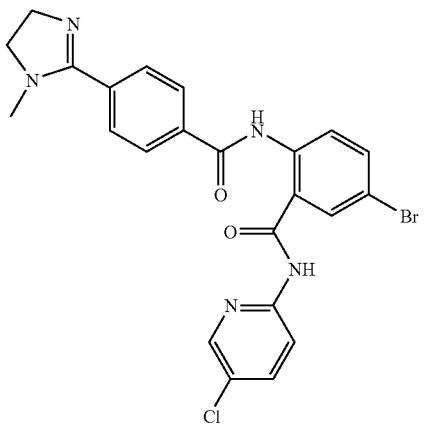

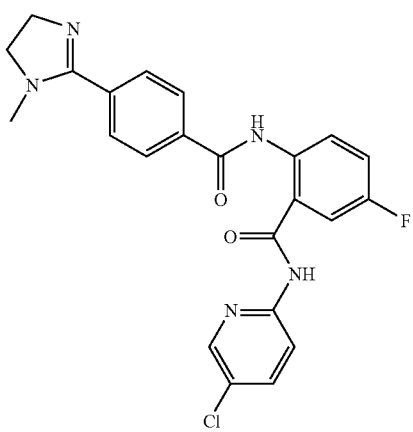

-continued
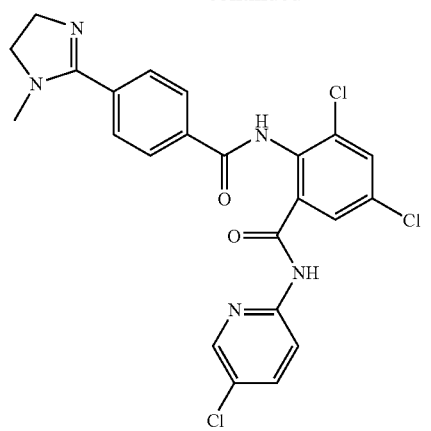
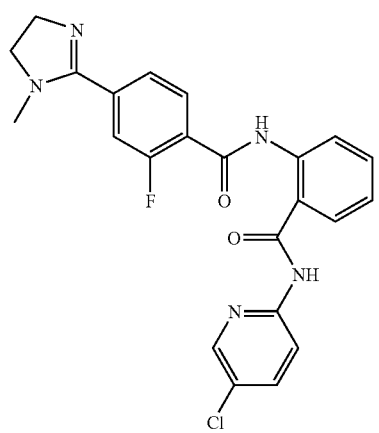
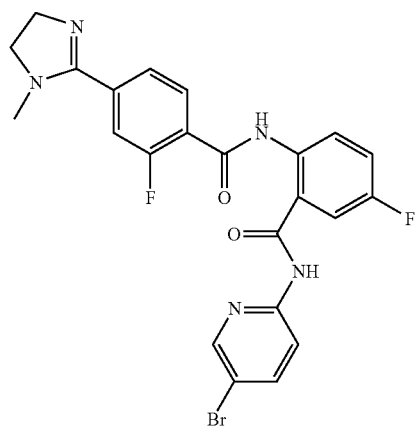
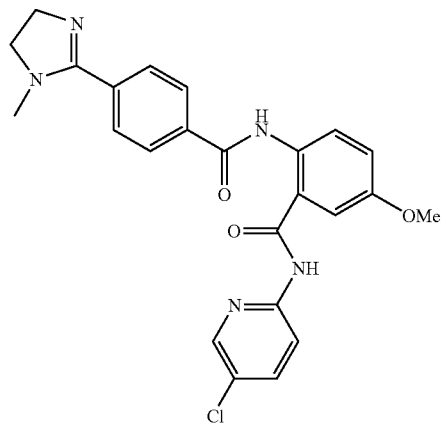
-continued
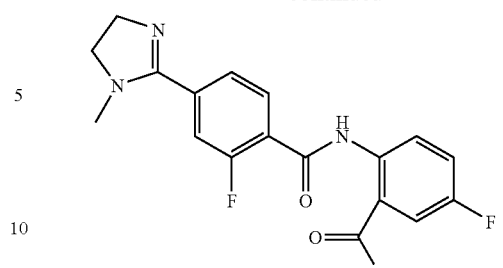
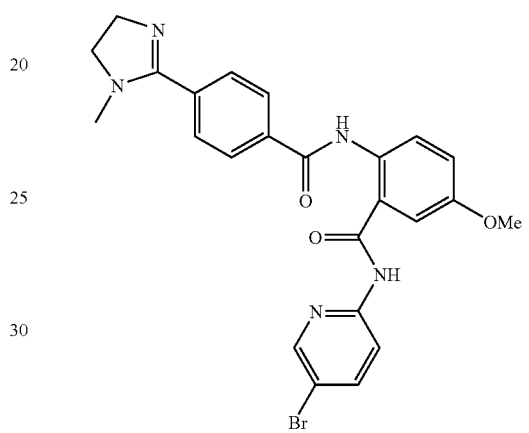
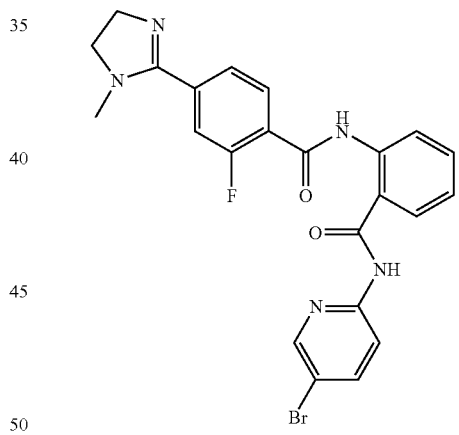
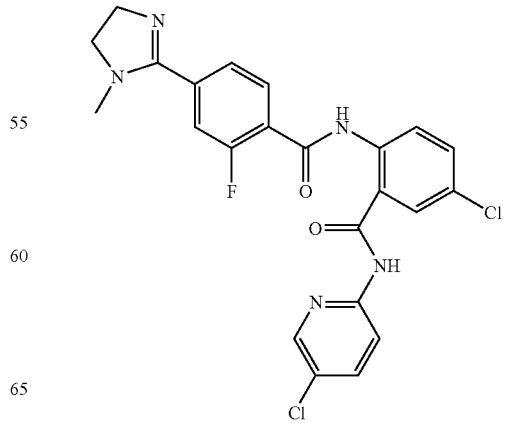

-continued
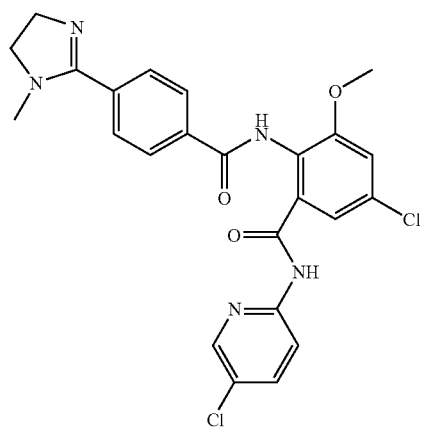
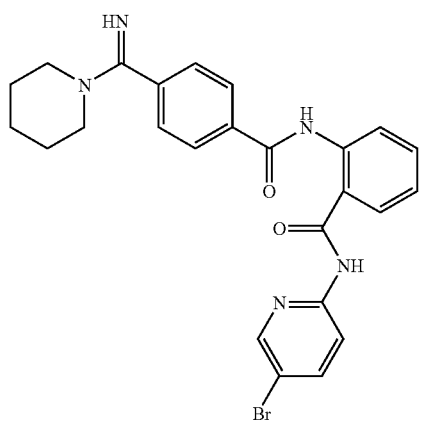
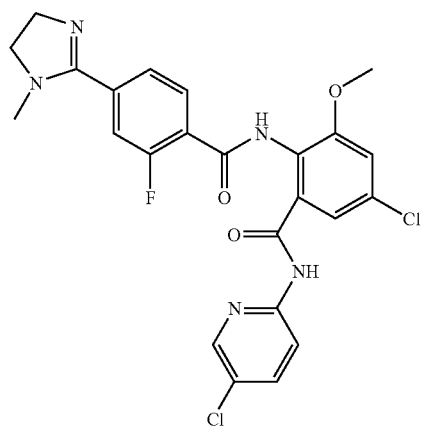
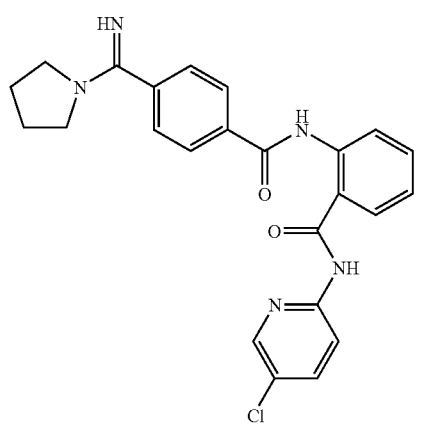
-continued
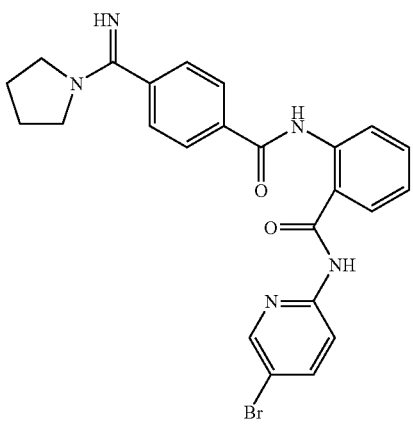
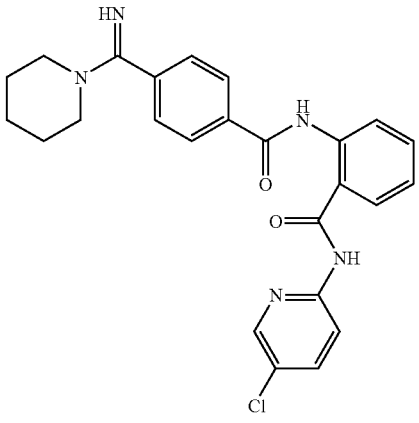
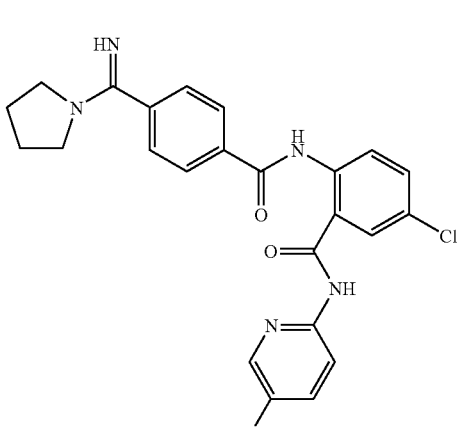
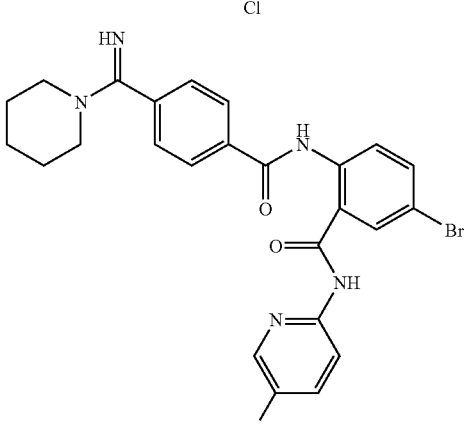

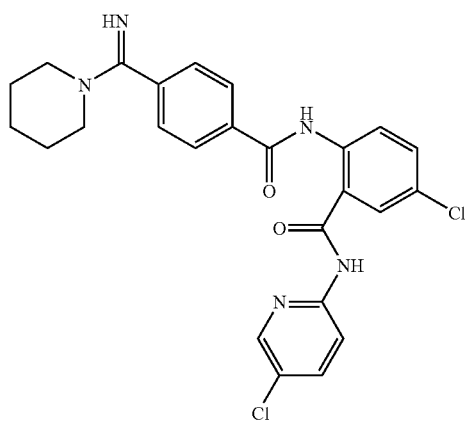
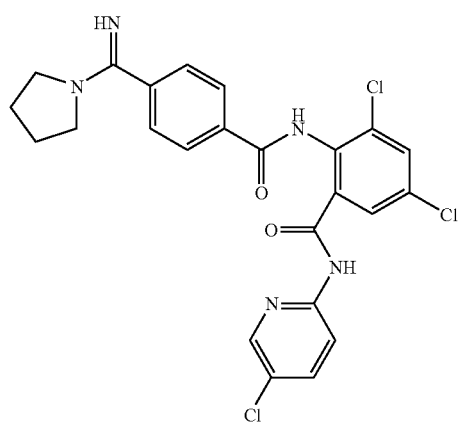
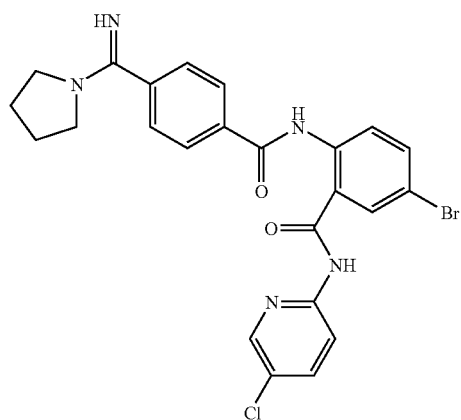
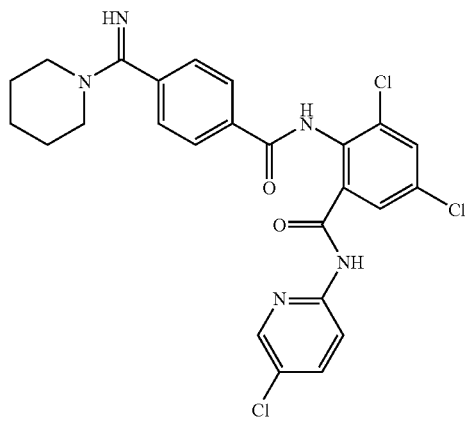
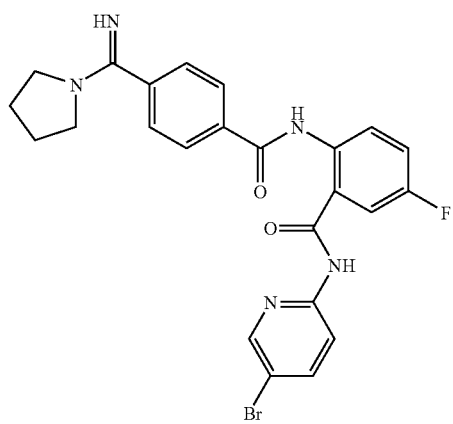
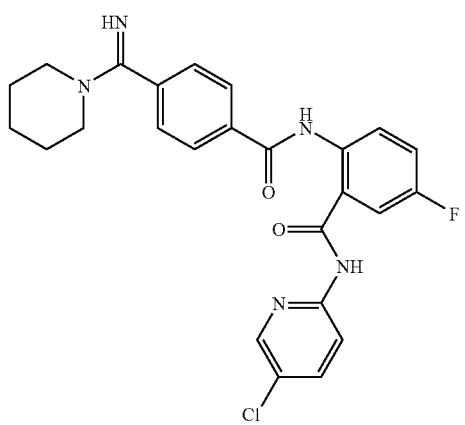
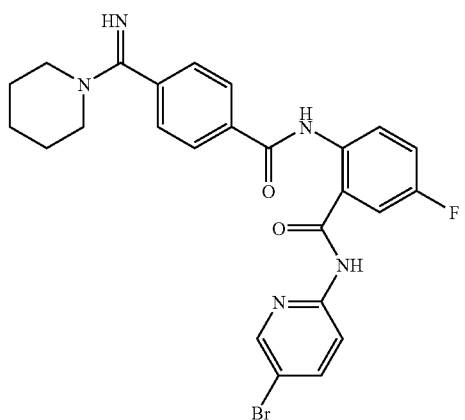
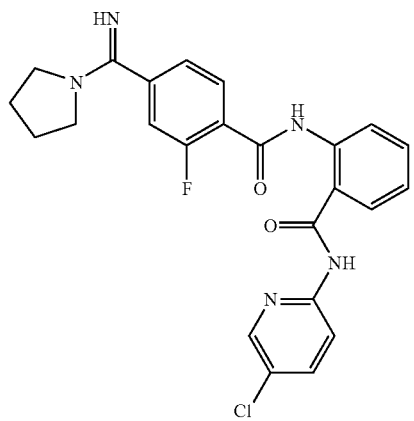

-continued
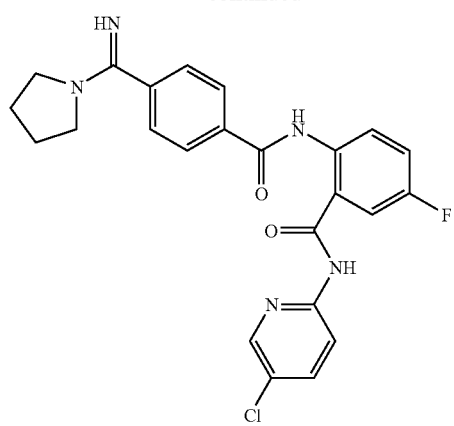
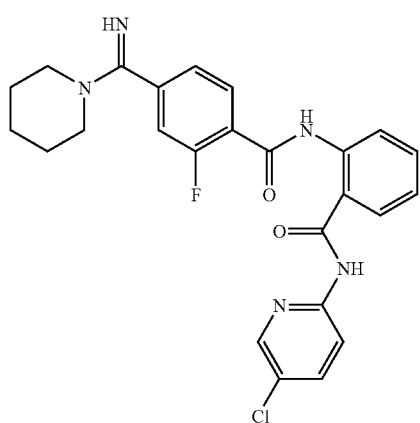
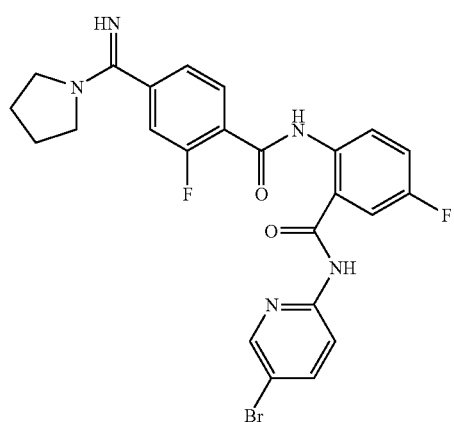
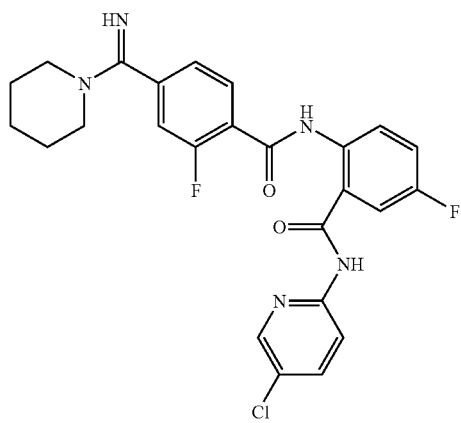
-continued
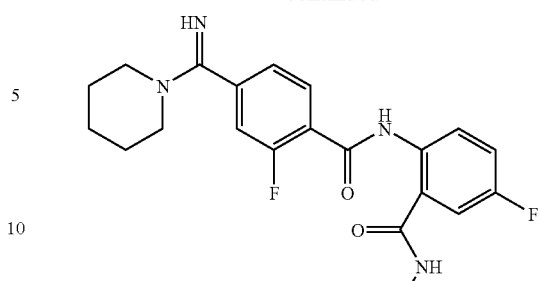
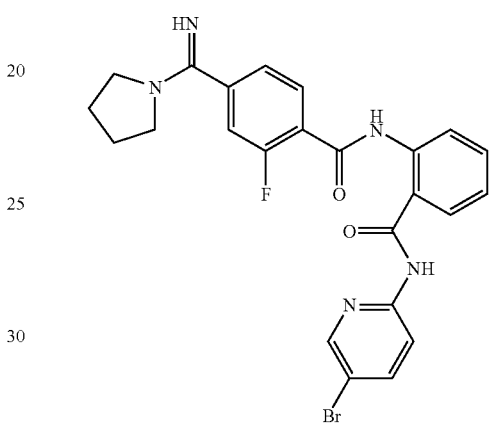
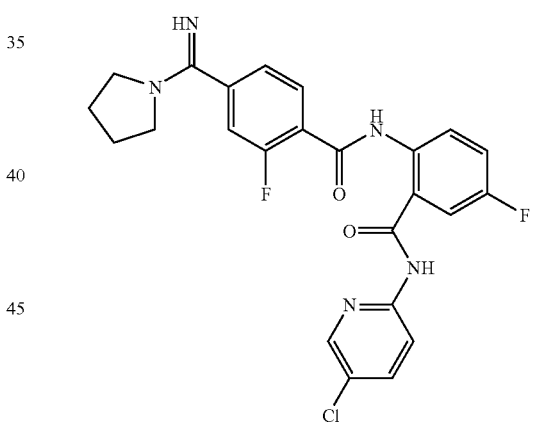
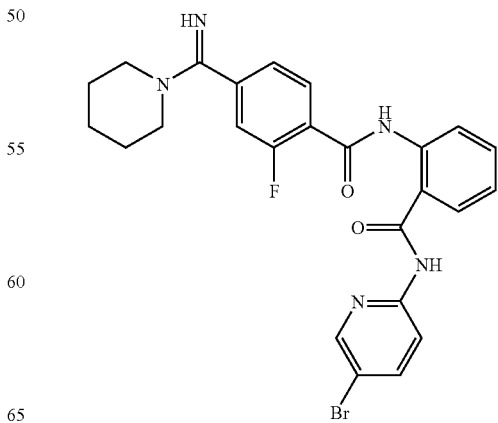

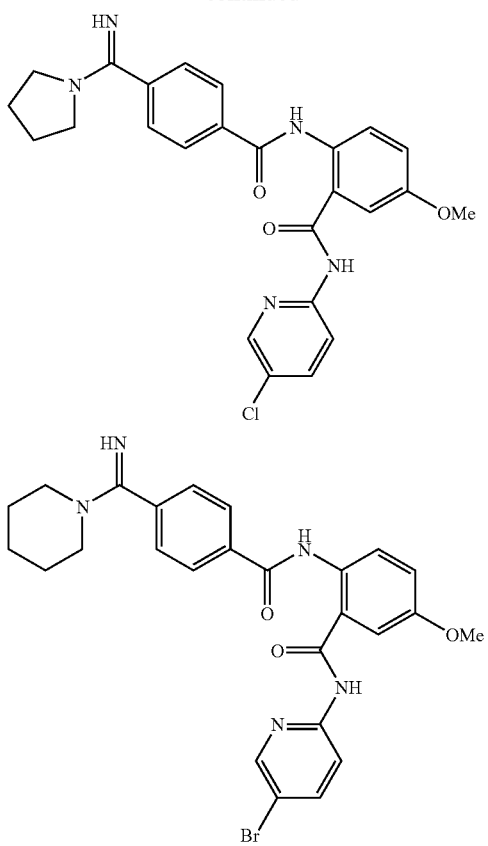

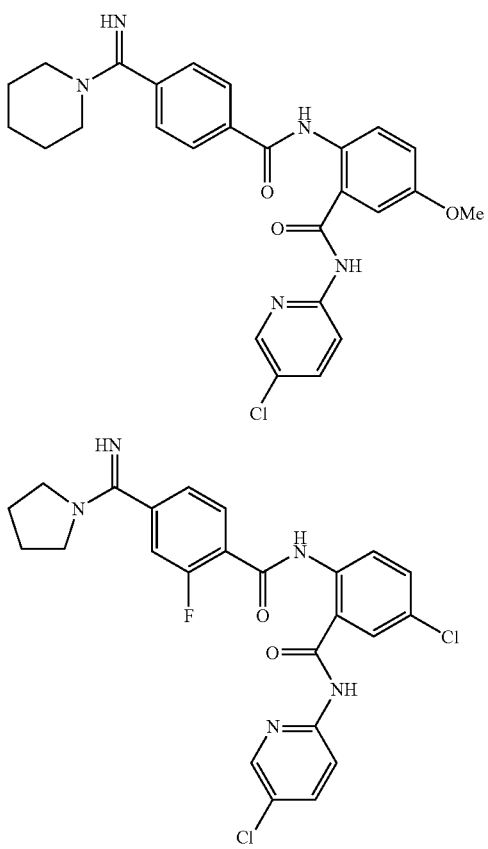

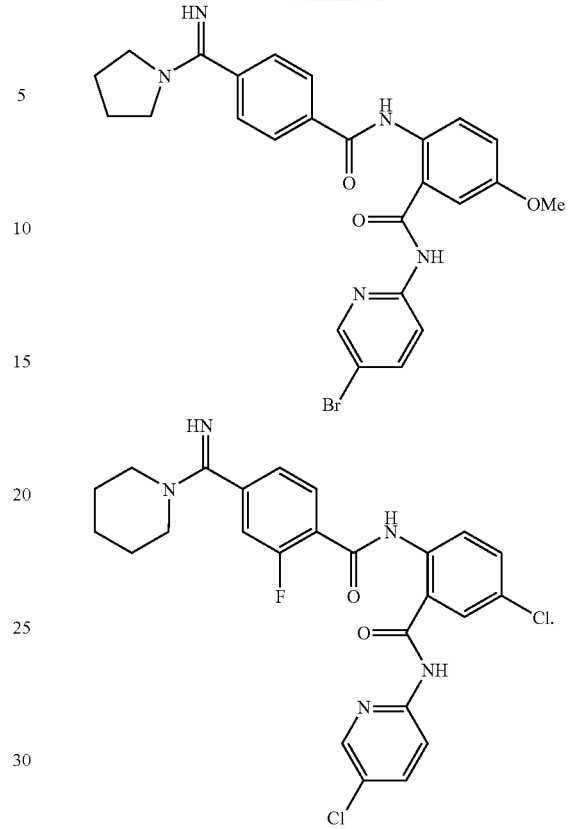

In further embodiments of the invention, the factor Xa inhibitors are compounds of Formula II:

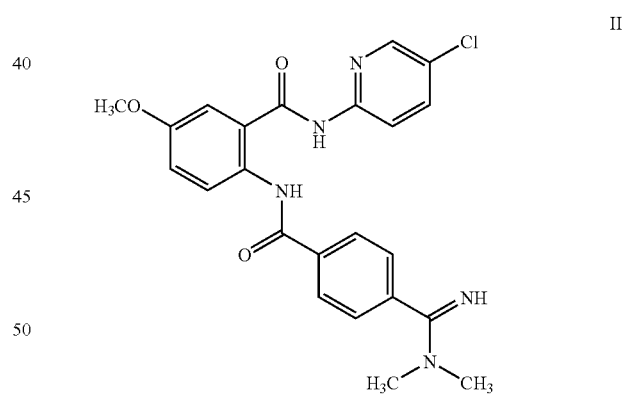

as well as all pharmaceutically acceptable isomers, salts, hydrates, solvates and prodrug derivatives thereof. Compounds of Formula II are disclosed as Example 206 in U.S. Pat. Nos. 6,376,515 and 6,835,739, both of which are incorporated by reference in their entirety herein. The compound of formula II has the generic name of betrixaban and is sometimes referred to this throughout.

In a specific embodiment, the salt of a compound of Formula II is a maleate salt. The maleate salt be formed by protonating one or more nitrogen atoms of the compound of Formula II. In one embodiment, the amidino nitrogen (=NH) of Formula II is protonated (=NH$_2^+$) to form the salt.

In one embodiment, the maleate salt of the compound of Formula II is represented by Formula III:

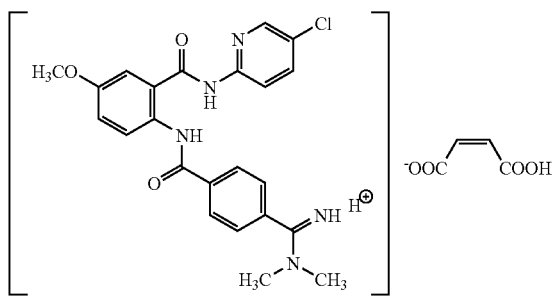

This is also referred to herein as betrixaban maleate.

In another embodiment, the present invention provides a salt of Formula III having a crystalline polymorph form. In some embodiments, the crystalline polymorph form exhibits a powder X-ray diffraction pattern having at least four and more preferably eight of the following approximate characteristic peak locations: 4.9, 9.7, 13.8, 14.1, 15.2, 17.6, 18.5, 20.8, 21.6, 22.7, 24.1, 26.3, 26.8 degrees 2θ. In still another embodiment, the powder X-ray diffraction pattern has approximate characteristic peak locations of 4.9, 9.7, 11.8, 13.8, 14.1, 15.2, 17.6, 18.5, 19.9, 20.8, 21.6, 22.7, 24.1, 25.0, 26.3, 26.8 degrees 2θ. The invention contemplates that the approximate characteristic peaks will have a deviation of up to about ±0.2 degrees 2θ. See PCT/US2006/43635, filed Nov. 7, 2006, incorporated by reference in its entirety herein, for further disclosure of salts and polymorphs of salts of the compound of Formula II.

4. FORMULATIONS

One embodiment of this invention is directed to a unit dose formulation. The unit dose formulation comprises a pharmaceutical composition comprising a factor Xa inhibitor as described above and a pharmaceutically acceptable carrier. The factor Xa inhibitor is present in an coagulation-inhibition effective amount which is typically between about 0.1 mg/kg and about 2.0 mg/kg. In certain embodiments, the dose is formulated to administered once or twice daily, such that the total amount per day is the coagulation-effective amount. In some embodiments, the unit dose formulation is for oral delivery.

In the management of thrombotic disorders the compounds and/or salts of this invention may be utilized in compositions such as tablets, capsules, lozenges, or elixirs for oral administration, suppositories, sterile solutions or suspensions or injectable administration, and the like, or incorporated into shaped articles. The method of administration will vary from subject to subject and be dependent upon such factors as the type of mammal being treated, its sex, weight, diet, concurrent medication, overall clinical condition, the particular compounds and/or salts employed, the specific use for which these compounds and/or salts are employed, and other factors which those skilled in the medical arts will recognize.

Capsules useful in the present invention can be prepared using conventional and known encapsulation techniques, such as that described in Stroud et al., U.S. Pat. No. 5,735, 105. The capsule is typically a hollow shell of generally cylindrical shape having a diameter and length sufficient so that the pharmaceutical solution compositions containing the appropriate dose of the active agent fits inside the capsule. The exterior of the capsules can include plasticizer, water, gelatin, modified starches, gums, carrageenans, and mixtures thereof. Those skilled in the art will appreciate what compositions are suitable.

In addition to the active agent, tablets useful in the present invention can comprise fillers, binders, compression agents, lubricants, disintegrants, colorants, water, talc and other elements recognized by one of skill in the art. The tablets can be homogeneous with a single layer at the core, or have multiple layers in order to realize preferred release profiles. In some instances, the tablets of the instant invention may be coated, such as with an enteric coating. One of skill in the art will appreciate that other excipients are useful in the tablets of the present invention.

Lozenges useful in the present invention include an appropriate amount of the active agent as well as any fillers, binders, disintegrants, solvents, solubilizing agents, sweeteners, coloring agents and any other ingredients that one of skill in the art would appreciate is necessary. Lozenges of the present invention are designed to dissolve and release the active agent on contact with the mouth of the patient. One of skill in the art will appreciate that other delivery methods are useful in the present invention.

Formulations of the compounds and/or salts of this invention are prepared for storage or administration by mixing the salt having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro Ed. 1985). Such materials are nontoxic to the recipients at the dosages and concentrations employed, and include buffers such as phosphate, citrate, acetate and other organic acid compounds and/or salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium, and/or nonionic surfactants such as Tween, Pluronics or polyethyleneglycol.

Dosage formulations of the compounds and/or salts of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide compounds and/or salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations (such as tablets, capsules and lozenges) and topical formulations such as ointments, drops and dermal patches. The sterile membranes of this invention are desirably incorporated into shaped articles such as implants which may employ inert materials such as biodegradable polymers or synthetic silicones, for example, Silastic, silicone rubber or other polymers commercially available.

The compounds and/or salts of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds and/or salts of this invention may also be delivered by the use of antibodies, antibody fragments, growth factors, hormones, or other targeting moieties, to which the salt molecules are coupled. The compounds and/or salts of this invention may also be coupled with suitable polymers as targetable drug carriers. Such polymers can include polyvinylpyrrolidinone, pyran copolymer, polyhydroxy-propyl-methacrylamide-phenol, polyhydroxyethyl-aspartamide-phenol, or polyethyleneoxide-polylysine substituted with palmitoyl residues. Furthermore, compounds and/or salts of the invention may be coupled to a class of biodegradable polymers useful in achieving controlled release of a drug, for example polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

5. COMPOUND PREPARATION a. Salts of the Compound of Formula II

The compound of Formula II can be converted to salts of various inorganic and organic acids including, but not limited to, HCl salt, lactate, maleate, phenoxyacetate, propionate, succinate, adipate, ascorbate, camphorate, gluconate, phosphate, tartrate, citrate, mesylate, fumarate, glycolate, naphthalene-1,5-disulfonate, gentisate and benzene sulfonate. One of skill in the art will recognize that other acids can be used to make salts comprising the compound of Formula I that are useful in the present invention. It is also contemplated that salts of the invention can be readily converted to other salts of the invention.

A number of methods are useful for the preparation of the salts described above and are known to those skilled in the art. For example, reaction of the compound of Formula II with one or more molar equivalents of the desired acid in a solvent or solvent mixture in which the salt is insoluble, or in a solvent like water after which the solvent is removed by evaporation, distillation or freeze drying. Alternatively, the compound of Formula II may be passed over an ion exchange resin to form the desired salt or one salt form of the product may be converted to another using the same general process.

The compound of Formula II was prepared according to the procedure set forth below. The maleate salt of the compound of Formula II was chosen for its excellent crystallinity, thermal and hydrolytic stability, and high purity.

b. Betrixaban

The compound of Formula II or betrixaban can be prepared according to any of several different methodologies, either on a gram scale (<1 kg) or a kilogram scale (>1 kg). A gram-scale method is set forth below in Example 2. Another gram-scale method is set forth in U.S. Pat. No. 6,844,367B1, see Example 266, which is hereby incorporated by reference in its entirety.

Alternatively, the compound of Formula II can be prepared on a kilogram scale using the procedure set forth in Example 2. The formation of the dimethyl amidine of Formula II involves nucleophilic attack on a cyano group by a deprotonated amine, with the deprotonated amine formed from a secondary amine and an alkyl lithium. As used herein, the term "alkyl" refers to a hydrocarbyl radical of from 1 to 8 carbon atoms. One of skill in the art will recognize that the deprotonated amine can be formed via other methods, and formation of the amidine functionality of Formula II can be prepared by a variety of other methods.

A useful solvent for the method of the present invention as described above is a aprotic solvent such as tetrahydrofuran (THF), diethyl ether, dimethoxymethane, dioxane, hexane, methyl tert-butyl ether, heptane, and cyclohexane. In addition, the formation of the deprotonated amine can be carried at temperatures below 10° C. The nucleophilic addition of the amine to form the compound of Formula I can also be carried out at temperatures below 10° C. One of skill in the art will recognize that the methods of the present invention can be practiced using various other solvents, reagents, and reaction temperatures.

In addition while the method of the present invention for preparing the compound of Formula II on a gram-scale is similar to the procedure used on the kilogram-scale, there is an increase in the scale of the reaction of more than 3400%. Moreover, in several steps increased yields are obtained using reduced amounts of the excess reagents. One of skill in the art will recognize that the compound of Formula I can be prepared via other chemical methodologies on both a gram and kilogram scale.

EXAMPLES

Unless stated otherwise, the abbreviations used throughout the specification have the following meanings:

Å=Angstrom
A %=total percent area
aq.=aqueous
cm=centimeter
d=doublet
DSC=differential scanning calorimetry
EDTA=ethylenediaminetetraacetic acid
eq. equivalent
EtOH=ethanol
g=gram
HPLC=high performance liquid chromatography
hr=hour
Hz=Hertz
IR=infrared
J=coupling constant
kg=kilogram
kV=killivolts
L=liter
LOD=limit of detection
M=molar
m=multiplet
mA=milliampere
Me=methyl
MeO=methoxy
MeOH=methanol
mg=milligram
min.=minute
mL=milliliter mm=millimeter
MTBE=methyl tert-butyl ether
N=normal
nM=nanomolar.
NMR=nuclear magnetic resonance
s=singlet
TDS=total dissolved solids
TGA=thermal gravimetric analysis
THF=tetrahydrofuran
μM=micromolar
BID=twice daily Example 1

Preparation of a Crystalline Polymorph Salt of Formula III a. Gram Scale Preparation In a 3-necked 1500 mL round bottomed flash equipped with a condenser, free base compound of Formula I (25 g; 1 eq.) was charged and 9:1 EtOH/Water (500 mL) was added while stirring. The resulting slurry was heated to 70° C. Maleic acid (12.77 g; 2 eq.) was added dropwise as a solution (100 mL of 9:1 EtOH/Water) and after 50 mL had been added, the solution became noticeably clearer. On complete addition of the maleic acid solution the temperature was held at 80° C. for 5 minutes. The vessel was allowed to cool slowly to 45° C. and 400 mL of MTBE was then added. The solution was stirred for another 12 hr. The resulting precipitate was filtered and dried under vacuum. The maleate salt of the compound of Formula I was recovered in a 45% yield (14.2 g).

b. Kilogram Scale Preparation

The compound of Formula I (24.6 kg) was charged into a 760 L GLMS reactor (Reactor A). Maleic acid (12.7 kg, 2.0 eq), ethanol (445 kg, 18.1 parts), and high purity water (140 kg, 5.7 parts) were added. The reaction mixture was adjusted to 22° C. (19-25° C.) and agitated at that temperature for ca. 1 hr, then transferred through a polishing filter into a conditioned 780 L Hastelloy reactor (Reactor B). The Reactor A pump and lines were rinsed forward into Reactor B with additional ethanol (ca. 45 kg) via polishing filter. The filtrate was concentrated under vacuum with a maximum temperature of warm glycol bath (to heat reactor jacket) of 45° C., until ca. 140 L (5.7 parts volume) remained. The Reactor B contents were sampled for in-process NMR, which showed that the mole ratio of ethanol:the maleate salt of the compound of Formula I was 26. High purity water (49 kg, 2.0 parts) was charged to Reactor B and concentration under vacuum resumed until a pot volume of ca. 140 L (5.7 parts volume) was achieved. In-process NMR indicated that the mole ratio of ethanol:the maleate salt of the compound of Formula I was 14. High purity water (49 kg, 2.0 parts) was again charged and concentration under vacuum resumed to obtain a pot volume of ca. 140 L. In-process NMR showed that the mole ratio of ethanol:the maleate salt of the compound of Formula I was 5. The temperature of the Reactor B contents were adjusted to 22° C. (19-25° C.) and formation of a slurry was visually confirmed. The reaction mixture was agitated at 22° C. (19-25° C.) for ca. 2 hrs, and then filtered onto a 30" centrifuge fitted with a filter cloth. The Reactor B pump and lines were rinsed forward to the 30" centrifuge via polishing filter with two portions of high purity water (ca. 30 kg each). The filter cake was sampled for in-process HPLC, which showed that the purity of the product was 99.1 A %, the largest impurity was 0.26 A %, and therefore recrystallization was unnecessary. The filter cake (33.1 kg) was dried under vacuum with a maximum temperature of warm glycol bath (to heat dryer jacket) of 40° C. After ca. 30.5 hrs, in-process LOD analysis indicated a solvent content of 0%. The dry product was discharged (26.4 kg) and stored at 2-8° C. The yield for the final product was slightly higher than expected at 85% (expected 50-80%). Purity of the maleate salt was measured by the presence of hydrolyzed amidine content as measured by HPLC, and the purity was found to be >99%.

$^1$H NMR (DMSO-$d_6$): δ 3.0 (s, 3H), 3.2 (s, 3H), 3.82 (s, 3H), 7.2 (d, 1H, J=9.0 Hz), 7.42 (s, 1H), 7.68 (d, 1H, J=8.0 Hz), 7.95-8.15 (m, 2H), 8.12 (m), 8.18 (m, 1H), 8.42 (s, 1H), 9.0 (s, 1H), 11.0 (s, 1H), 11.2 (s, 1H); IR (KBr, cm$^{-1}$): 3300, 1685, 1600, 1515, 1380, 1270, 1200, 1100, 1050, 880, 800, 710.

Example 2

Preparation of the Compound of Formula II

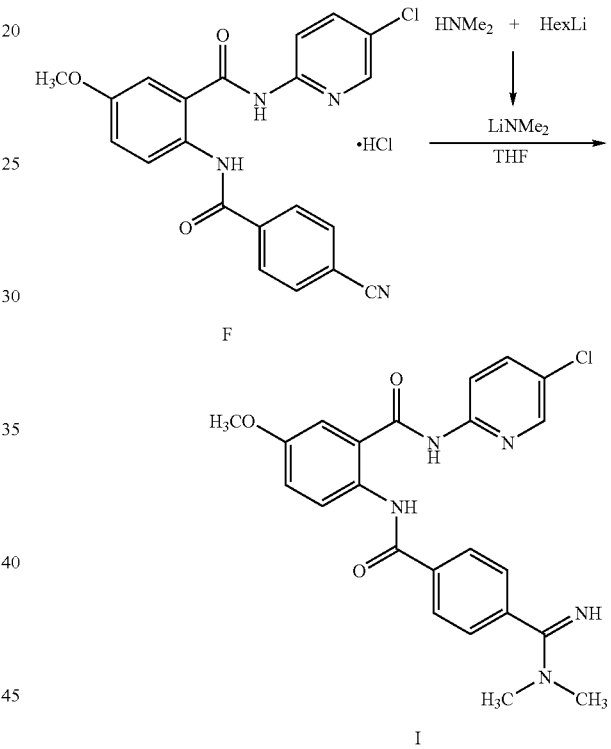

a. Gram Scale Preparation

A slurry of the compound of Formula F (455 g, 1.0 eq.) in THF (4.67 kg, 10.3 parts) was prepared and adjusted to <10° C. Lithium dimethyl amide was prepared as follows: hexyllithium (2.3 N/hexane, 2.45 L, 5.5 eq.) was added to dimethylamine solution (2 N/THF, 2.8 L, 5.5 eq.) maintaining<10° C. The lithium dimethyl amide solution was charged into the slurry containing the compound of Formula F keeping the pot temperature of <10° C. The reaction progress was monitored by in-process HPLC which confirmed that the amount of Formula F was <1.0 A %. A buffer solution of NaHCO$_3$ (490 g, 1.1 parts, 5.7 eq.) and Na$_2$CO$_3$ (490 g, 1.1 parts, 4.5 eq.) in deionized water (6.6 kg, 14.51 parts) was prepared, and the above reaction mixture was transferred to this aqueous solution maintaining <5° C. The product precipitated out and the resulting slurry was adjusted to 20° C. over a period of 12 hr. The solid was filtered, and the resulting wet cake was washed with 3.5 kg (7.7 parts) of deionized water. The solid was filtered off using a coarse frit glass bench filter, and rinsed forwarded with cold (0-5° C.) absolute ethanol (628 g, 1.4 parts). The product was dried at 30-35° C. Dry product was obtained in 458 g (73% yield).

b. Kilogram Scale Preparation

A slurry of the compound of Formula F (31.5 kg, 1.0 eq.) in THF (251 kg, 8.0 parts) was prepared in a 780 L Hastelloy reactor (Reactor A) and adjusted to 0° C. (−3 to 3° C.). 2 M Dimethylamine in THF (161.0 kg, 5.0 eq.) and THF (63 kg, 2 parts) were charged into a 1900 L GLMS reactor (Reactor B) and adjusted to 0° C. (−3 to 3° C.) with maximum agitation. Hexyllithium (2.3 M, 97.2 kg, 4.5 eq.) was slowly charged to Reactor B while maintaining a max temperature of 10° C. The pump and lines were rinsed forward to Reactor B with THF (3.2 kg). The Reactor B contents were adjusted to 0° C. (−3 to 3° C.), then transferred to Reactor A while keeping Reactor A temperature ≦10° C. The Reactor B pump and lines were rinsed forward with THF (31.4 kg, 1.0 part). The Reactor A contents were adjusted to 0° C. (−3 to 3° C.), and agitated at this temperature until the reaction was complete as verified by HPLC (1-2 hrs). After about 1 hr of agitation, in-process HPLC analysis indicated that 0 A % starting material remained (in-process criteria: max 1 A %). Reactor A contents were adjusted to −5° C. (−8 to −3° C.). In-process cleaning of Reactor B with water was performed. Two previously prepared aqueous solutions (NaHCO$_3$ (35.0 kg, 1.1 parts) in water (236 kg, 7.5 parts), and Na$_2$CO$_3$ (35.0 kg 1.1 parts) in water (236 kg, 7.5 parts)) were charged to Reactor B and adjusted to −3° C. (0 to 6° C.). Reactor A contents were transferred to Reactor B through an insulated line, maintaining the temperature of Reactor B at −8° C. to a maximum of 5° C. The Reactor A pump and lines were rinsed forward with cold [−5° C. (−8 to −3° C.)] THF (31.4 kg, 1.0 part). Reactor B contents were adjusted to 22° C. (19-25° C.) and agitated for ca. 3 hrs. Slurry formation was visually confirmed, and Reactor B contents were filtered onto a 30" centrifuge fitted with a filter cloth. The Reactor B pump and lines were rinsed forward onto the 30" centrifuge fitted with a filter cloth with drinking water (63 kg, 2 parts). The wet filter cake (66.5 kg) was transferred back to Reactor B and submitted to a slurry wash in drinking water (1005 kg, 32 parts) at 22° C. (19-25)° C. for ca. 1 hr. The product was filtered onto the 30" centrifuge (after in-process cleaning and fitting with a filter cloth), and the Reactor B lines and pump were rinsed forward with drinking water (63 kg, 2 parts). The water rinse was sampled for test by TDS, which was found to be 0.46%. The Reactor B pump, lines and wet filter cake were further rinsed with cold [0° C. (−3 to 3° C.)]ethanol (44 kg, 1.39 parts). The wet filter cake was dried under vacuum with a maximum temperature of water bath (to heat dryer jacket) of 35° C. In-process LOD was 0% after ca. 24 hrs of drying, and the product was discharged (24.8 kg) in 76.7% yield. HPLC showed 98% purity, with dechlorinated impurity at 1.14%.

Example 3

Preparation of the Compound of Formula F

Step 1. Synthesis of 2-nitro-N-(5-chloro-pyridin-2-yl)-5-methoxy-benzamide (C)

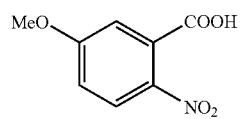

A

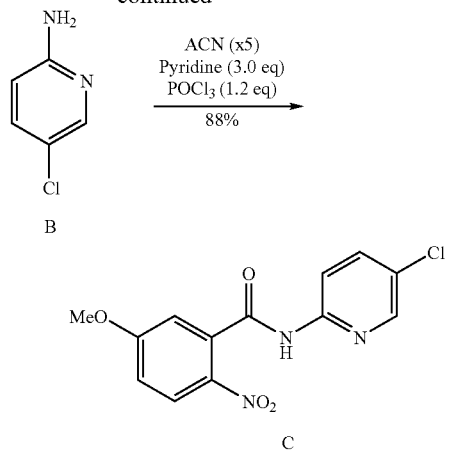

5-Methoxy-2-nitrobenzoic acid (A) (25.0 kg, 1.0 eq.), 2-amino-5-chloropyridine (B) (16.3 kg, 1.0 eq.), and acetonitrile (87.5 kg, 3.5 parts) were charged to a 380 L GLMS reactor. The reaction mixture was adjusted to 22° C. (19-25° C.) and anhydrous pyridine (30.0 kg, 3.0 eq.) was added. The pump and lines were rinsed forward with acetonitrile (22.5 kg, 0.9 parts), and the reactor contents were adjusted to a temperature of 19-22° C. Phosphorous oxychloride (23.3 kg, 1.20 eq.) was charged to the contents of the reactor via a metering pump, while maintaining a temperature of 25° C. (22-28° C.). The metering pump and lines were rinsed forward with acetonitrile (12.5 kg, 0.5 parts), while keeping the temperature at 25° C. (22-28° C.). The reaction mixture normally turned from a slurry to a clear solution after the addition of about ⅓ of the POCl$_3$. At the end of the addition, it became turbid. After complete addition, the reaction mixture was agitated at 25° C. (22-28° C.) for ca. 1 hr, at which time HPLC analysis confirmed reaction completion. The solution was cooled to 15° C. (12-18° C.) and drinking water (156.3 kg, 6.25 parts) was charged slowly while keeping reaction temperature of between 12 and 30° C. The reaction mixture was then adjusted to 22° C. (19-25° C.) and agitated for ca. 5 hrs until exotherm ceased. Formation of a slurry was visually confirmed and the contents of the reactor were filtered onto a pressure nutsche fitted with a filter cloth. The reactor, pump, and lines were washed forward onto the pressure nutsche with two portions of drinking water (62.5 kg, 2.5 parts each). The filtrate had a pH value of 7. The product (41.8 kg) was dried under vacuum with a maximum temperature of water bath (to heat dryer jacket) of 50° C. After ca. 12 hrs, in-process LOD analysis indicated a solvent content of 0.72%. The dry product (C) was discharged (34.4 kg) with 88.2% yield and 99.1% purity by HPLC.

Step 2. Synthesis of 2-amino-N-(5-chloro-pyridin-2-yl)-5-methoxy-benzamide (D)

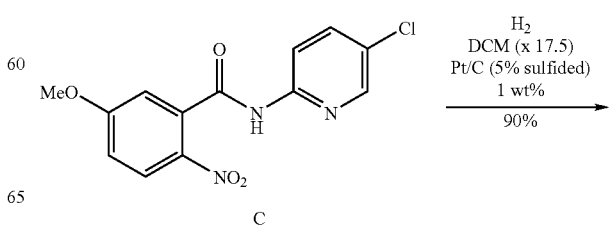

C

43

-continued

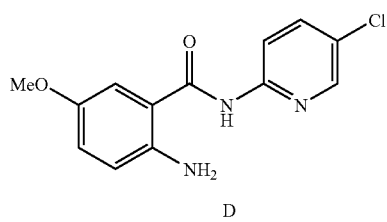

D

To a 780 L Hastelloy reactor, compound C (33 kg, 1.0 eq.), 5% platinum carbon (sulfided, 0.33 kg, 0.010 parts) and dichloromethane (578 kg, 17.5 parts) were charged. Agitation was started and reactor contents were adjusted to 22° C. (19-25° C.). The reactor was pressurized with ca. 30 psi hydrogen and the reaction mixture gently heated to 28° C. (25-31° C.). Hydrogenation of the reactor contents was performed under ca. 30 psi at 28° C. (25 to 31° C.; maximum 31° C.) until the reaction was complete by HPLC. After 16.5 hrs, the reaction was deemed complete after confirming the disappearance of starting material (0.472 A %). The contents of the reactor were circulated through a conditioned celite pad (0.2-0.5 kg celite conditioned with 20-55 kg dichloromethane) prepared in a 8" sparkler filter to remove the platinum catalyst. The reactor and celite bed were rinsed forward with two portions of dichloromethane (83 kg, 2.5 parts each). The filtrate was transferred to and concentrated in a 570 L GLMS reactor under a atmospheric pressure to ca. 132 L (4 parts volume). Ethanol (69 kg, 2.1 parts) was charged and concentration continued under atmospheric pressure to ca. 99 L (3 parts volume). In-process NMR indicated that the dichloromethane content was 39%. Ethanol (69 kg, 2.1 parts) was charged again and concentration continued again to ca. 99 L (3 parts volume). In-process NMR indicated that the dichloromethane content was 5%. The reaction mixture was then adjusted to 3° C. (0 to 6° C.), agitated for ca. 1 hr, and the resulting slurry filtered onto a jacketed pressure nutsche fitted with a filter cloth. The reactor, pump, and lines were rinsed forward with cold [3° C. (0-6° C.)]ethanol (26 kg, 0.8 parts). The wet filter cake (36.6 kg) was dried under vacuum at 40-50° C. with a maximum temperature of water bath (to heat dryer jacket) of 50° C. LOD analysis after 12.5 hrs indicated solvent content was at 0.1%. The dry product (D) was discharged (26.4 kg) in 89.5% yield. HPLC showed 98.4 A % purity, with dechlorinated impurity at 0.083%.

Step 3. Synthesis of N-(5-chloro-pyridin-2-yl)-2-(4-cyano-benzoyl-amino)-5-methoxy-benzamide Hydrochloride (F)

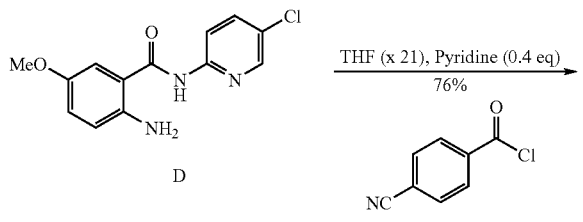

44

-continued

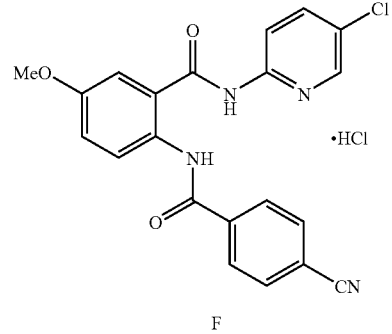

F

To a 780 L Hastelloy reactor, was charged 4-cyanobenzoyl chloride (E) (17.2 kg, 1.1 eq.) and THF (92 kg, 3.5 parts). Reactor contents were agitated at 22° C. (19-25° C.) until all of the solids had dissolved. The resulting solution was transferred to a lower receiver and the reactor was rinsed forward with THF (26 kg, 1 part). Compound D (26.4 kg, 1 eq.), THF (396 kg, 15 parts) and pyridine (2.90 kg, 0.4 eq.) were charged to a clean reactor. The pump and lines were rinsed forward with THF (34 kg, 1.3 parts). Via a metering pump, the 4-cyanobenzoyl chloride/THF solution was charged to the reactor, keeping the temperature at ≦30° C. and rinsing forward with THF (ca. 10 kg). The resulting yellow-colored slurry was agitated at 22° C. (19-25° C.) for ca 2 hrs. In-process HPLC taken after 2 hrs showed a compound of Formula D content of 0%, indicating completion of the reaction. The slurry was filtered onto a pressure nutsche fitted with a filter cloth. The reactor, pump, lines and wet cake were rinsed with three portions of ethanol (ca. 15 kg each). The wet filter cake was discharged (65.4 kg) and transferred back to the reactor for slurry wash in ethanol (317 kg, 12 parts) at 22° C. (19-25° C.) for ca. 1 hr. The slurry was filtered onto the pressure nutsche and the reactor, pump, lines, and wet filter cake were rinsed with two portions of ethanol (ca. 15 kg each) and two portions of THF (ca. 15 kg each). The wet filter cake was dried under vacuum with a maximum temperature of warm glycol bath (to heat the dryer jacket) of 40° C. After 14.5 hrs of drying, LOD was 0.75%. The dried material was milled (screen 0.125") to give 31.8 kg of product, which was dried under vacuum for another 10.5 hrs. LOD after drying was 1.8%, and the product was discharged (31.5 kg) in 74.8% yield (expected 60-90%). HPLC showed 100% purity.

Example 4

Bioassay to Determine Antithrombotic Activity

This example describes an in vitro assay to determine antithrombotic activity in vivo. The predictive value of the assay has been verified using an established in vivo baboon model described below. The compound used in the assay corresponds to a compound of Formula II or a salt thereof.

Materials and Methods

For the in vitro studies, a plasma pool was generated from blood collected via venipuncture into 3.2% (1:9 v/v) tri-sodium citrate from a minimum of ten donors. The specific thrombin substrate used was Z-GGR-AMC (Bachem). Tissue factor (Innovin, "TF") was purchased from Dade Behring. Rabbit anti-human TF IgG and purified recombinant human TF were from American Diagnostica. COATEST LMW Heparin/Heparin Kits were from Chomogenix. Source of anticoagulants tested were as follows: enoxaparin sodium (Aventis Pharmaceuticals), fondaparinux sodium (Glaxo Smith Kline), bivalirudin (The Medicines Company), fXa inhibitor C921-78 (Betz, A. et al. *Biochem.*, 1999; 38-14582-14591); rivaroxaban and razaxaban.

Thrombin generation in the plasma pool in the absence and presence of various anticoagulants and in warfarin treated patients was initiated by the addition of Innovin and calcium. Thrombin generation was measured by the continuous signal generated by cleavage of thrombin substrate over a 10 min period in a FlexStation fluorescence reader (Molecular Probes). The fluorescence signal (Max-Min relative fluorescence units) is presented as units (RFU) or arbitrary unites (AU) of thrombin generation and anti-fXa units were measured by Coatest. Quantitation of TF concentration in Innovin was carried out by immunoblotting with rabbit anti-human TF IgG, followed by densitometry and comparison with purified human TF (residues 1-263, expressed in baculovirus).

For the ex vivo validation of the assay, plasma was collected from 168 patients receiving anticoagulation therapy. Subjects comprised medically stable hospital inpatients or those attending an outpatient's clinic and who were receiving warfarin (no change to warfarin dose for approximately 7 days). Blood was only collected if venesection and the routine measurement of traditional anti-coagulations tests (INR, aPTT etc.) was already intended and no additional needle-sticks were performed for this study. An additional 5 mL of blood was collected and placed in sodium citrate-anticoagulated tubes. Samples were then twice centrifuged to collect the plasma fraction, and this plasma was then promptly stored at −80° C.

Results

The assay was sensitive to anticoagulants with varying mechanisms of action. Addition of unfractionated heparin (UFH) or low molecular weight heparin (LMWH) to healthy donor plasma produces a dose-dependent inhibition in the assay. Similarly, direct thrombin or fXa inhibitors also elicit a dose proportional inhibitory activity. The effect of specific inhibitors of thrombin or factor Xa on TF-induced plasma thrombin generation is shown in the Table 1.

TABLE 1

| Drug | $IC_{50}$ |
|---|---|
| Fondaparinux | 160 nM |
| Thrombin inhibitor Bivalirudin | 2.4 µg/mL |
| fXa inhibitor C921-78 | 17 nM |
| fXa inhibitor Rivaroxaban | 80 nM |
| fXa inhibitor Razaxaban | 125 nM |

Figure 1B:
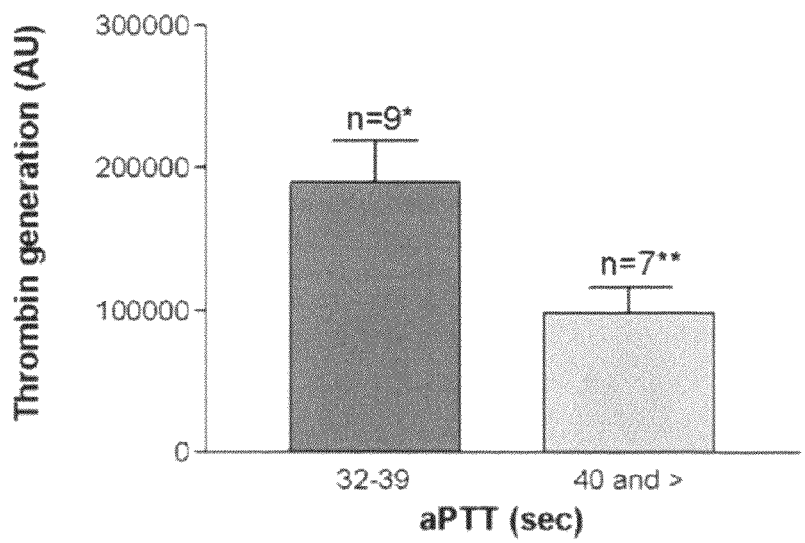
FIG. 1B shows the correlation of thrombin generation with activated partial thromboplastin time (aPTT) in anticoagulated patients treated with enoxaparin. Plasma thrombin generation was measured in 16 enoxaparin-treated patients. Anti-fXa units were measured by COATEST LMW assay according to the manufacturer's instructions. Groups were compared by Student's t-test.
Figure 1C:
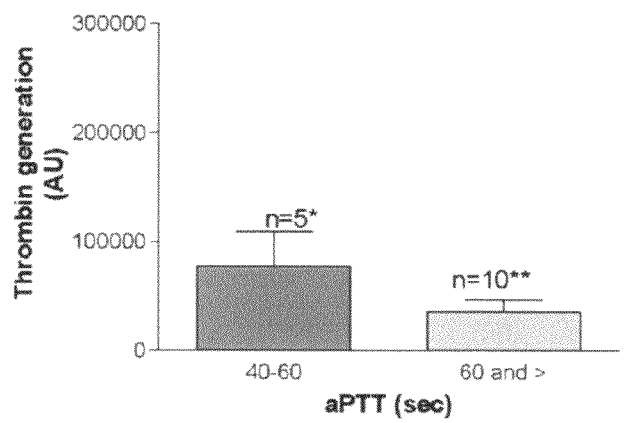
FIG. 1C shows the correlation of thrombin generation with aPTT in anticoagulated patients treated with unfractionated heparin (UFH). Plasma thrombin generation was measured in 15 patients. Anti-fXa units were measured by COATEST LMW assay according to the manufacturer's instructions. Groups were compared by Student's t-test.

This assay is also useful for measuring anticoagulation in both acute and chronically anticoagulated patients. aPTT Measurements from patients treated with UFH or LMWH correlated with inhibition of thrombin generation. Relative to traditional markers of thrombin generation (TAT and F1.2 as measured by ELISA), this bioassay provided a superior correlation to INR measurements. The results of which is shown in FIGS. 1A, 1B and 1C. The extent of thrombin generation (AU) at 10 minutes was measured in plasma samples from (a) warfarin treated patients and plotted against INR values from 137 patients (FIG. 1A), (b) Enoxaparin-treated patients plotted against aPTT values from 16 patients (FIG. 1B) and (c) unfractionated heparin (UFH)-treated patients plotted against aPTT values from 15 patients (FIG. 1C).

Example 5

Comparison of Betrixaban to Fondaparinux

Evaluation in a whole blood prothrombinase assay was carried out to compare betrixaban to fondaparinux, an indirect inhibitor of fXa. Like fondaparinux, betrixaban dose-dependently inhibited platelet mediated prothrombinase activity in this test system.

Materials and Methods

Amidolytic assays for inhibition of purified human fXa and related proteases were carried out as reported previously (Sinha, U et al. *Eur. J. Pharmacol.* 2000; 114:2313-6). For determination of prothrombinase inhibitory activity, human plasma prethrombin-2 was purchased from Haematologic Technologies and the thrombin substrate Boc-Asp (OBzl)-Pro-Arg-AMC. HCl was obtained from Bachem. Data analysis for deriving kinetic parameters were carried out using the Dynafit software (Biokin). Betrixaban exhibited a Ki of 0.117 (nM) and a prothrombinase Ki of 0.801 (nM)

The assay described in Example 4 was employed. Betrixaban was tested in a model of thrombogenic device incorporation in an arteriovenous shunt in baboons (Hanson S R et al. *J. Clin. Invest.* 1993; 92:2003-12). The two component thrombogenic device measures thrombus growth on a dacron graft and an expansion chamber using $^{111}$In labeled platelets and $^{125}$I labeled fibrinogen. This model has been previously used to study a wide variety of anticoagulants (unfractionated and low molecular weight heparins, thrombin and fXa inhibitors).

Results

Dose-dependent inhibition of venous thrombosis was observed at four doses (0.05, 0.12, 0.21 and 0.49 mg/kg) of betrixaban. Ex vivo measurements of plasma thrombin generation, aPTT, PT, activated clotting time ("ACT"), and anti fXa units were performed during the time course. In contrast to the observed antithrombotic activity (30 to 89% inhibition of platelet deposition, 0 to 87% inhibition of fibrin deposition), there were minimal extension of clotting parameters upon betrixaban treatment. The results of this are presented in the Table 2 below.

TABLE 2

| | Fold Change from Control Mean ± SD | | |
|---|---|---|---|
| Agent | ACT | PT | aPTT |
| Control | 0.87 ± 0.09 | 1.00 ± 0.04 | 1.02 ± 0.03 |
| betrixaban 0.05 mg/kg | 1.14 ± 0.06 | 1.02 ± 0.03 | 1.07 ± 0.03 |
| betrixaban 0.12 mg/kg | 1.14 ± 0.15 | 1.05 ± 0.06 | 1.07 ± 0.03 |
| betrixaban 0.21 mg/kg | 1.11 ± 0.04 | 1.07 ± 0.03 | 1.09 ± 0.08 |
| betrixaban 0.49 mg/kg | 1.28 ± 0.06 | 1.17 ± 0.11 | 1.29 ± 0.21 |

Anti fXa units were below the limit of quantitation for the three lower doses and 0.31 Units/ml at the highest dose. Template bleeding times were not perturbed for any of the betrixaban treated animals. The ex vivo parameter that correlated to the antithrombotic activity was the dose proportional inhibition (correlation coefficient $R^2$=0.99) of plasma thrombin generation; which ranged from 13% inhibition at the lowest dose to 72% at the highest dose. Thus, this new prothrombinase bioassay predicts in vivo antithrombotic activity.

Table 3 below provides dose responsive inhibition of in vivo thrombosis in the baboon model. Table 3 also provides the anti-fXa activity in baboon plasma samples during infusion of the control or the test compound.

TABLE 3

| Dosed Group | Plasma Concentration Range of Betrixaban (ng/ml) | % Inhibition of Platelet Deposition | % Inhibition of Fibrin Formation |
|---|---|---|---|
| Control | 0 | 0.00 | 0.00 |
| 1 | 7-10 | 29.71 | −0.38 |
| 2 | 13-21 | 44.20 | 37.50 |
| 3 | 26-38 | 65.22 | 71.97 |
| 4 | 54-88 | 88.77 | 87.12 |

Figure 2:
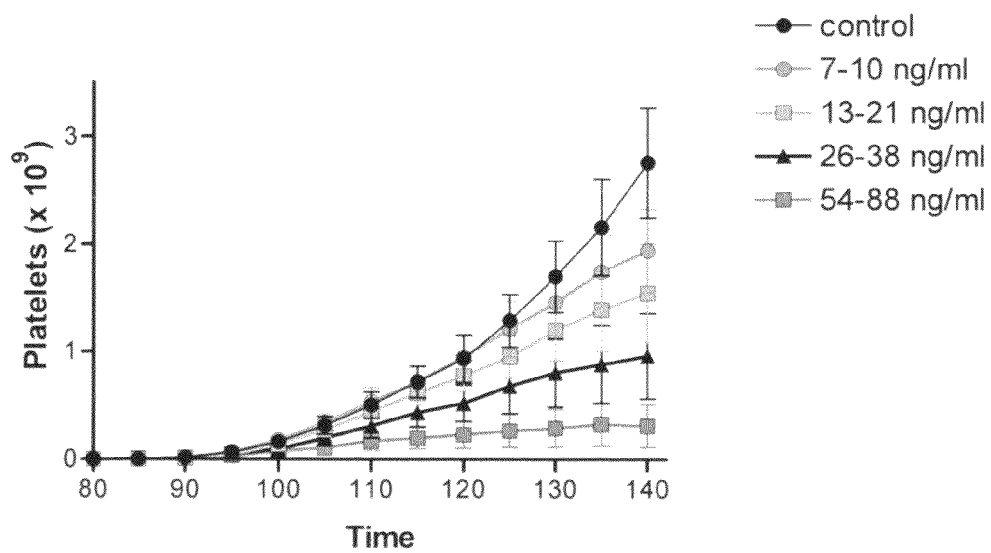
FIG. 2 shows the dose responsive inhibition of in vivo thrombosis in the baboon model and provides evidence that the in vitro assay is predictive of in vivo antithrombotic activity. Indium labeled platelet deposition in the chamber over time following infusion of vehicle or betrixaban. The number of labeled platelets in the chamber were normalized for pre-infusion platelet counts for individual animals. Data represent mean±standard deviation. Platelet deposition at 140 minutes was analyzed by ANOVA followed by Dunnett's post-test. Dose 3 (26-38 ng/ml) had a significant decrease compared to control (P<0.05) and dose 4 (54-88 ng/ml) had a significant decrease compared to control (P value<0.01).

FIG. 2 provides further evidence that the in vitro assay is predictive of in vivo anti-thrombotic activity. Specifically, FIG. 2 shows the dose responsive inhibition of in vitro thrombosis in the baboon model. Deposition of $^{111}$In labeled platelets over time in the venous chamber during infusion of betrixaban (n=3 at each dose). Control animals were infused with vehicle (n=4).

Figure 3:
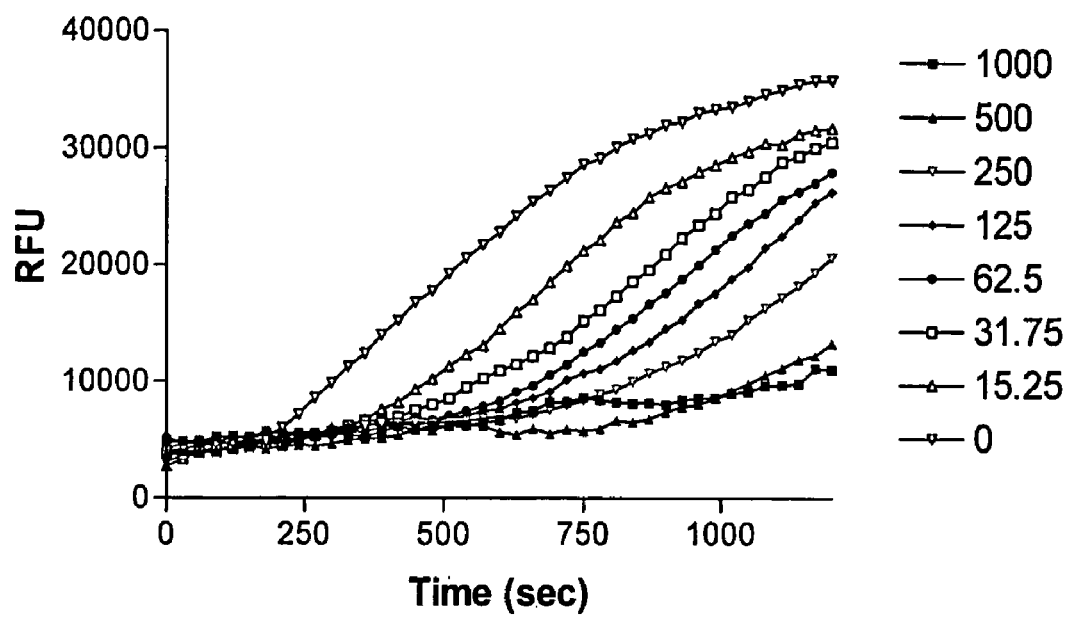
FIG. 3 shows dose responsive inhibition of thrombin generation in whole blood from healthy human volunteers. Whole blood was treated with the stated concentration (in nM) of betrixaban prior to initiation of test. Relative fluorescence units resulting from cleavage of labeled thrombin substrate is shown.
Figure 4A:
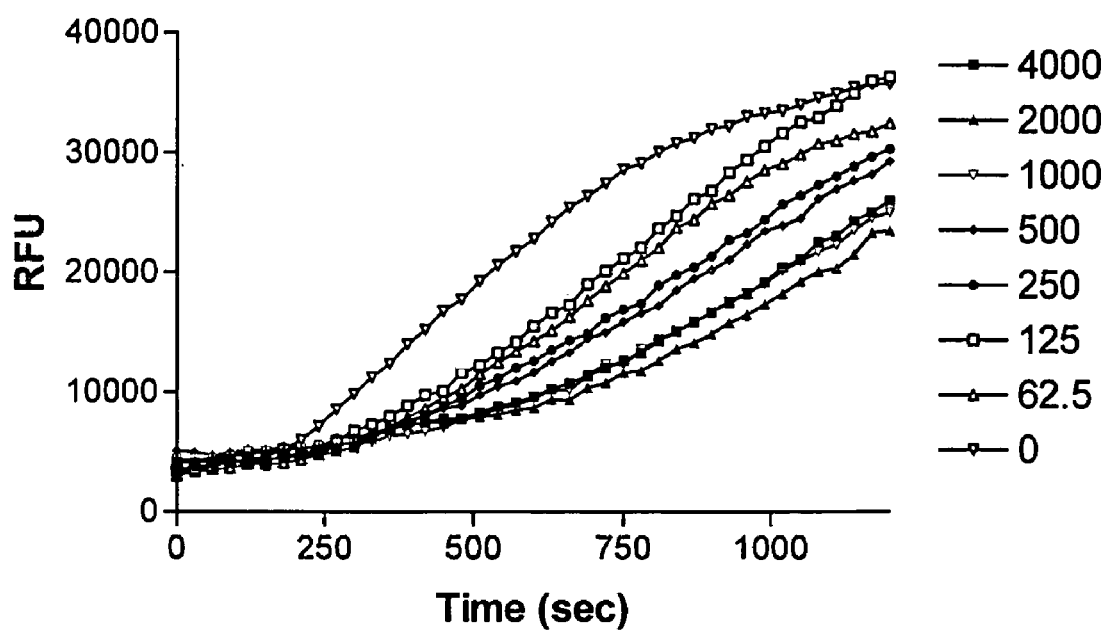
FIGS. 4A and 4B shows dose responsive inhibition of thrombin generation in whole blood from healthy human volunteers. Whole blood was treated with the stated concentration of fondaparinux (in nM) prior to initiation of test. The range of fondaparinux concentration depicted in FIG. 4B corresponds to levels of therapeutic anticoagulation used in orthopedic surgery and acute coronary syndrome patients. Relative fluorescence units resulting from cleavage of labeled thrombin substrate is shown.
Figure 4B:
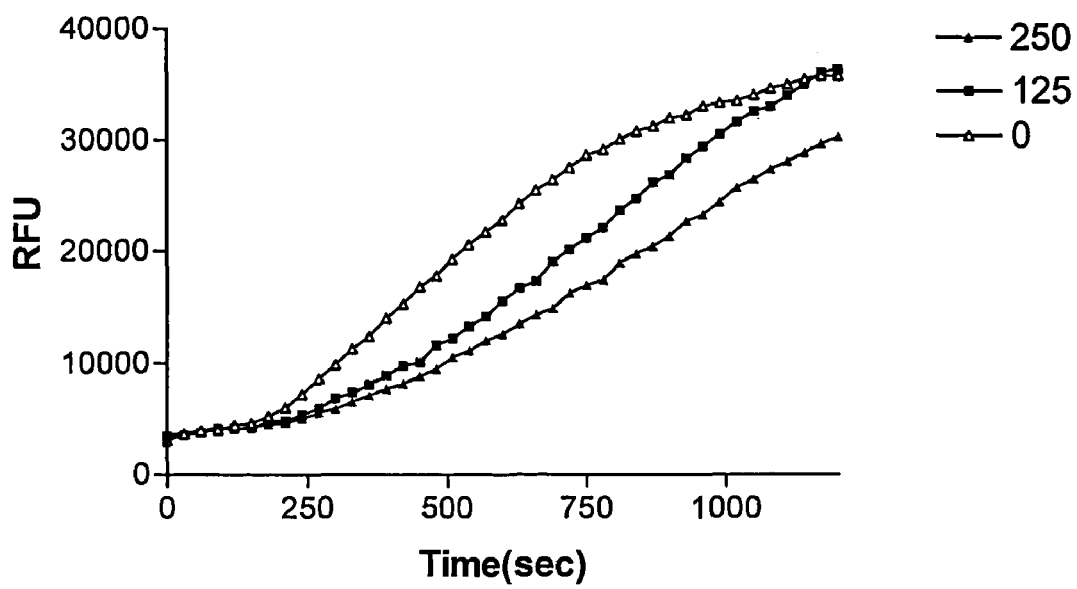

FIGS. 3, 4A, and 4B show the inhibition of tissue factor initiated thrombin generation in human whole blood by betrixaban compared with fondaparinux. Thrombin activity was quantitated by cleavage of the fluorogenic substrate. Dose response of inhibition of thrombin generation was measured by addition of varying amounts of betrixaban and fondaparinux to whole blood from eleven healthy donors. Relative fluorescence unit (RFU) measurements of representative donor is shown.

This study showed that in vitro and in vivo characteristics of betrixaban as a potent inhibitor of purified human fXa and the prothrombinase complex. Specifically, there was greater than 86,000 fold specificity against related human proteases such as thrombin and activated Protein C. There was also a dose-dependent inhibition of tissue factor initiated thrombin generation in human whole blood and a dose-dependent inhibition of on-going thrombosis in a primate model of arteriovenous thrombosis without extending clotting parameters or bleeding time. Thus, compared to standard measures of coagulation, this assay was more predictive of in vivo efficacy in the animal model.

Example 6

Inhibition of Prothrombinase and Not Soluble Factor Xa Predicts Efficacy of fXa Inhibitors in an In Vivo Model of Deep Vein Thrombosis (DVT)

This example was designed to test the hypothesis that the potency of fXa inhibitors against fXa incorporated into the prothrombinase complex would predict in vivo antithrombotic efficacy. Eight fXa inhibitors from four structurally distinct chemical series with a range of activities against fXa were tested for their ability to inhibit the prothrombinase enzyme complex in human plasma. Thrombin generation and subsequent cleavage of a specific thrombin substrate was used as a measure of prothrombinase activity, inhibitory activity being defined by the concentration of inhibitor required to produce a 2-fold extension in the time to maximal thrombin production (2× lag). In vitro rabbit PT times were also determined. In vitro rabbit prothrombin times (PT) were determined by addition of thromboplastin to rabbit plasma. Inhibition in the rabbit DVT model was assessed as previously described (Hollenbach et al., *Thromb. Haemost.* 1994; 71:357) and related to plasma concentrations of drug.

Materials and Methods

Compounds were synthesized (Zhu et al; *Curr. Top. Med. Chem.* 2001; 2:101-119; Betz et al. *Biochem.*, 1999; 36:14582-91)). The concentration of compound required to inhibit the amidolytic activity of purified soluble human fXa (*Haematologic Technologies*) by 50% ($IC_{50}$) was measured by following the formation of p-nitroaniline from the peptide substrate Z-D-Arg-Gly-Arg pNA (Diapharma) at 405 nm in a Spectramax plate reader (Molecular Devices) (Sinha et al., *Eur. J. Pharmacol.* 2000; 395:51-59). Thrombin formation by prothrombinase was assessed in Reptilase®-treated pooled human platelet poor plasma by measuring p-nitroaniline at 405 nm following cleavage of the peptide thrombin substrate Pefachrome TG (Pentapharm) (Sinha et al., *ATVB;* 2003; 23:1098-1104). The concentration of compound which elicited a two-fold increase in the time of maximal thrombin generation was recorded as the 2× lag concentration. Antithrombotic efficacy against rabbit venous thrombosis was determined by measuring the thrombus accretion on a cotton thread placed in the vena cava by means of a catheter inserted into the left femoral vein. The decrease in thrombus weight following a two hour infusion of compound was expressed relative to vehicle control (Hollenbach et al., *Thromb. Haemost.* 1994; 71:357).

Drug concentrations in rabbit plasma were measured by LC-MS/MS. Rabbit prothrombin times were measured using Thromboplastin C Plus (Dade) on an automated coagulation timer (ACL 3000, Instrumentation Laboratory) (Sinha, et al., *Eur. J. Pharmacol.*, 2000; 395:51-59).

Results

All compounds inhibited soluble fXa by 50% at concentrations less than 10 nM. However, the rank order of potencies for inhibition of soluble fXa differed from that required to inhibit the prothrombinase complex. The results are shown in Table 4.

TABLE 4

| No. | Cmpd Class | fXa $IC_{50}$ (nM) | Prothrombinase 2× lag (μM) | Plasma Concentration in DVT (μM) | Thrombosis Inhibition (%) | Rabbit PT 2× change (μM) |
|---|---|---|---|---|---|---|
| 1 | Ketothiazole | 0.5 | 0.18 | 0.06 | 94 | 7 |
| 2 | Anthranilamide | 1.3 | 0.22 | 1.14 | 37 | 2.7 |

TABLE 4-continued

| No. | Cmpd Class | fXa IC$_{50}$ (nM) | Prothrombinase 2x lag (µM) | Plasma Concentration in DVT (µM) | Thrombosis Inhibition (%) | Rabbit PT 2x change (µM) |
|---|---|---|---|---|---|---|
| 3 | Anthranilamide | 0.7 | 0.24 | 1.65 | 47 | 1.7 |
| 4 | Anthranilamide | 0.4 | 0.25 | 1.04 | 47 | 1.0 |
| 5 | Anthranilamide | 0.8 | 0.34 | 3.39 | 41 | 1.5 |
| 6 | naphthalenepyrazole | 4.4 | 0.92 | 5.2 | 11 | 4.7 |
| 7 | 1,2-Benzenediaine | 3.5 | 1.35 | 4.6 | 19 | 8.8 |
| 8 | Isoxazole | 8.2 | 1.66 | 9.2 | 0 | 64 |

There was also poor correlation between the 2× lag value for prothrombinase inhibition and the concentration required to achieve a 2× change in rabbit PT ($R^2$=0.57). Neither the activities of fXa inhibition nor the change in rabbit PT predicted activity in the in vivo deep vein thrombosis (DVT) model. In contrast, compounds could be broadly divided into 3 levels of efficacy for inhibition of in vivo thrombus growth depending on their potency in the in vitro prothrombinase assay. Compound I had the lowest 2× lag value of 0.18 µM and was the most potent inhibitor of in vivo thrombosis with 94% inhibition at a plasma concentration of 65 nM. The second group of compounds, with 2× lag values in the prothrombinase assay ranging from 0.22 to 0.34 µM, inhibited in vivo thrombus formation by 37 to 47% at plasma concentrations ranging from 1.04 to 3.39 µM. Compounds in the third category were the least potent prothrombinase inhibitors (2× lag values greater than 0.92 µM) and were unable to significantly inhibit in vivo thrombosis even at plasma concentrations of 9.2 µM. These data show that the 2× lag value obtained in the prothrombinase assay, and not inhibition of soluble fXa or extension of rabbit PT time, is most predictive of fXa inhibitor efficacy in the in vivo rabbit DVT model.

Given the limitations of current anti-coagulants, the position of factor Xa (fXa) at the convergence of both the extrinsic and intrinsic pathways of blood coagulation has made it an attractive target for the development of new therapies. With respect to investigating the structural-activity-relationship (SAR) of potential fXa inhibitors, assays measuring inhibition of solution phase fXa protease activity are an obvious starting point. However, the ability of compounds to inhibit soluble, purified fXa is not a true reflection of the interaction between inhibitor and enzyme in vivo. This is because the greatest contribution of fXa to the coagulation process occurs when it is combined with factor Va as part of the prothrombinase complex whereupon protease activity is increased 300,000 fold relative to solution-phase fXa. This increased activity of fXa in the prothrombinase complex is much harder to inhibit, thus any assessment of compound anti-fXa potency should include an evaluation of prothrombinase inhibition. Prothrombinase activity can be measured in platelet poor plasma (PPP) and, under these conditions, also takes into account the effect of plasma protein binding on compound potency. Another more direct way of assessing the effect of compounds on the anti-coagulation process is through the use of in vitro clotting assays such as prothrombin time (PT) and activated partial thromboplastin time (aPTT).

Example 7

Evaluation of Bioassay in Multiple Ascending Dose Study

Figure 5:
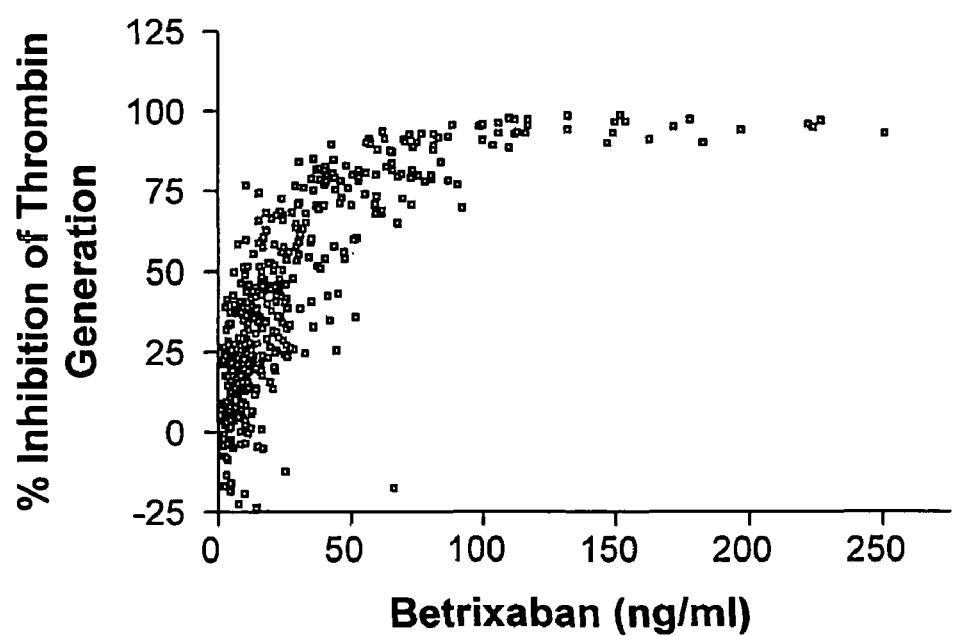
FIG. 5 shows data from in vitro assays performed with plasma from healthy human volunteers orally dosed with betrixaban. This is more thoroughly discussed in Example 8.

FIG. 5. shows data from in vitro assays performed with plasma from healthy human volunteers orally dosed with betrixaban. Nine subjects each received 40, 80 or 120 mg drug capsules every 12 hours for ten consecutive days. Control subjects (12) were treated with placebo or non-anticoagulant drug control. Plasma samples obtained from the subjects were evaluated in the in vitro biological assay of tissue factor initiated thrombin generation. Plasma samples were also analyzed for drug concentration using high-performance-liquid-chromatography with tandem mass spectrometry. Results show dose responsive correlation between plasma drug concentration of betrixaban and inhibition of thrombin generation in the biological assay.

Example 8

Human Therapeutic Concentrations of Betrixaban

Thrombin generation assays were performed as described in Example 4, with compounds added ex vivo to human whole blood. PT and aPTT values in various species determined from compounds added to platelet poor plasma. Samples were run on an ACL 3000plus (Coulter), PT determined using Dade® Thromboplastin C plus and aPTT determined using Dade® Actin® FS Activated PTT reagent.

Betrixaban and fondaparinux, an indirect fXa inhibitor, both significantly inhibited TAT and F1.2 generation in human whole blood. Compared to a therapeutic level of fondaparinux (200 nM), betrixaban (200 nM) was more potent in suppressing both markers of thrombin generation.

Materials and Methods

Multiple doses of betrixaban were evaluated in three animal models. The first model, which measured clot accretion on cotton threads placed in rabbit abdominal vena cava, compared inhibition of thrombus mass by betrixaban to that of supratherapeutic doses of enoxaparin (a LMW heparin).

The second model compared the ability of betrixaban to maintain vessel patency under arterial flow conditions in $FeCl_3$ induced thrombosis in rat carotid artery to that achieved by enoxaparin or clopidogrel (an antiplatelet agent).

The third model investigated inhibition of $^{111}$In labeled platelet deposition on dacron grafts and expansion chambers placed in femoral arteriovenous shunts in baboons. In all models tested, betrixaban and enoxaparin were administered as IV infusions and clopidogrel was dosed orally for three days. Ex vivo PT and aPTT were measured in all models. The models encompass stringent criteria of arterial and venous thrombosis and betrixaban produced dose-responsive antithrombotic activity in each of the three models. The efficacy of betrixaban compared favorably to supratherapeutic levels of enoxaparin and clopidogrel.

Efficacy in rabbit venous thrombosis was determined by measuring the thrombus accretion on cotton threads placed in the vena cava by means of a catheter inserted into the left femoral vein, as described by Hollenbach et al., *Thromb. Haemost.* 1994; 71:357-362, incorporated by reference in its entirety herein. The decrease in thrombus weight following a two hour infusion of compound was expressed relative to vehicle control. See also Sinha, et al., *Eur. J. Pharmacology.* 395:51-59 (2000), incorporated by reference in its entirety herein.

Rat $FeCl_3$ model adapted from Kurz, K. D. et al. *Thromb. Res.* 1990; 60(4):269-280, incorporated by reference in its entirety herein, utilizing the left carotid artery. A stenosis of the artery was applied with a silk ligature reducing blood flow by 50% with a light crush injury followed by application of 50% $FeCl_3$ for the duration of the experiment. Blood flow was monitored via pulsed Doppler flow probe and recorded for 90 minutes post-$FeCl_3$ application. Enoxaparin and Betrixaban administered IV. Clopidogrel administered orally Q.D. for 3 days.

The baboon model was performed at Oregon Health & Science University following procedures described by Hanson, S. R. et al. *J. Clin. Invest.* 1993; 92:2003-2012, incorporated by reference in its entirety herein. Briefly, thrombosis is induced by two different thrombogenic devices incorporated within an excorporeal femoral artery-vein (A-V) shunt. Arterial model utilizes a high shear stress environment to promote thrombus formation on a dacron graft. Venous model utilizes a low-shear stress environment to promote thrombus formation in an expansion chamber. Platelets and fibrin are pre-labeled with $^{111}In$ and $^{125}I$ fibrinogen to measure platelet deposition and fibrin accumulation, respectively.

Results

Surprisingly, unlike in the rodent models, efficacy in primates was attained at a much lower dose with minimal prolongation of PT. Species specificity was also demonstrated by in vitro extensions of PT and aPTT in rat, rabbit, baboon and human plasma. A 2x change of PT was attained at concentrations of 8.9, 1.6, 1 and 0.4 µM respectively. The data indicate that doses of betrixaban that inhibit thrombin generation in human blood and that provide anticoagulation similar to baboon dosed at 0.05-0.49 mg/kg may be sufficient to prevent venous thrombosis in humans. Comparative modeling of extents of change in PT to levels of antithrombotic efficacy also leads us to predict that human therapeutic activity for betrixaban may be attained without concurrent changes in ex vivo clotting parameters. The data is presented in Table 5.

TABLE 5

| Model of Thrombosis | Agent, Dose | Antithrombotic Activity | APTT fold change | PT fold change |
|---|---|---|---|---|
| Rabbit Vena Cava | betrixaban, 3 mg/kg | 76% inhibition | 2.22 | 2.34 |
| | Enoxaparin, 2.2 mg/kg | 96% inhibition | 2.06 | 1.01 |
| Rat Carotid | betrixaban, 19.1 mg/kg | 90% patency | 1.69 | 2.20 |
| | Enoxaparin, 7.6 mg/kg | 70% patency | 3.49 | 1.19 |
| | Clopidogrel, 3 mg/kg/day | 80% patency | 1.03 | 1.01 |
| Baboon Arteriovenous | betrixaban, 0.49 mg/kg | 90% inhibition (venous) 32% inhibition (arterial) | 1.29 | 1.17 |

Example 9

Comparison of Betrixaban with Enoxaparin in a Randomized Trial for the Prevention of Venous Thromboembolic Events after Total Knee Replacements This study included 215 patients undergoing total knee replacement (TKR) were randomized in a 2:2:1 ratio to either betrixaban 15 mg or 40 mg dose orally twice a day or enoxaparin (Enox) 30 mg dosed subcutaneously twice a day for 10 to 14 days. The study was blinded to the 15 versus 40 mg dose, but not to betrixaban vs. Enox. The primary efficacy endpoint was the incidence of venous thromboembolism ("VTE") (symptomatic or asymptomatic deep vein thrombosis on a mandatory unilateral venogram or symptomatic pulmonary embolism) through Day 10 to 14. Safety endpoints included the incidence of major and clinically significant nonmajor bleeds through the day after venography. All efficacy and bleeding endpoints were adjudicated by a blinded, independent central adjudication committee.

Materials and Methods

Betrixaban in this study was administered in gelatin capsules. The capsules contained betrixaban maleate, dextrose monohydrate, and magnesium stearate.

The initial dose of betrixaban was taken 6 to 8 hours after surgery and twice daily (BID) thereafter. Enoxaparin was administered subcutaneously 12 to 24 hours after surgery and every 12 hours (q 12 h) thereafter. Treatment continued for 10 to 14 days unless a protocol-specified stopping criterion had been met. After discharge from the hospital, patients self-administered study medication. The last dose of study medication was administered the morning of the scheduled mandatory venography of the operated leg (Day 10 to 14).

Blood samples for assessment of plasma drug concentrations and pharmacodynamic measurements were obtained at screening, 1 to 4 hours after administration of the morning dose of study medication on Day 2, on the day of discharge and prior to the mandatory venogram on Day 10 to 14. Plasma samples were analyzed for betrixaban using high-performance-liquid-chromatography with tandem mass spectrometry. The method was validated for a range from 0.100-50.0 ng/mL, based on the analysis of 0.2 mL plasma. Quantitation was performed using a calibration standard curve generated from weighted least square regression analysis.

Anticoagulation was measured by a thrombin generation inhibition assay as discussed in Example 4 and anti-Xa activity in addition to activated partial thromboplastin time (aPTT), prothrombin time (PT) and international normalized ratio (INR). The anti-Xa unit assay was adapted from the Coatest LMW heparin kit (Diapharma) and modified to a 96-well plate format. In this assay, standards and patient samples were assayed in duplicate and the limit of quantification was 0.05 anti-Xa U/mL. Thrombin generation was initiated by the addition of tissue factor (Innovin, Dade Behring) and calcium to citrate anticoagulated patient plasma (0.1 mL). Formation of thrombin was measured by cleavage of a specific thrombin substrate (Z-GGR-AMC, Bachem) over a 10 minute period. Relative fluorescence units were measured in a FlexStation fluorescence reader (Molecular Devices) and used for quantitation of thrombin generation. All patient plasma samples were assayed in triplicate and inhibition of thrombin generation reported as change from baseline relative fluorescent unit for each individual.

Results

A dose- and concentration-dependent effect of betrixaban on inhibition of thrombin generation and anti-fXa levels was observed. 175 Patients (81.4%) had an efficacy and safety assessment as shown in Table 6.

TABLE 6

| Primary efficacy and safety outcomes | betrixaban 15 mg BID | betrixaban 40 mg BID | Enox 30 mg BID |
|---|---|---|---|
| VTE % (95% CI) | 20 (12-32) | 15 (8-27) | 10 (3-23) |
| Major Bleeds % (95% CI) | 0 (0-4) | 0 (0-4) | 2 (0-12) |
| Clinical signif. nonmajor bleeds | 0 (0-4) | 2 (0-8) | 5 (1-16) |

Figure 6:
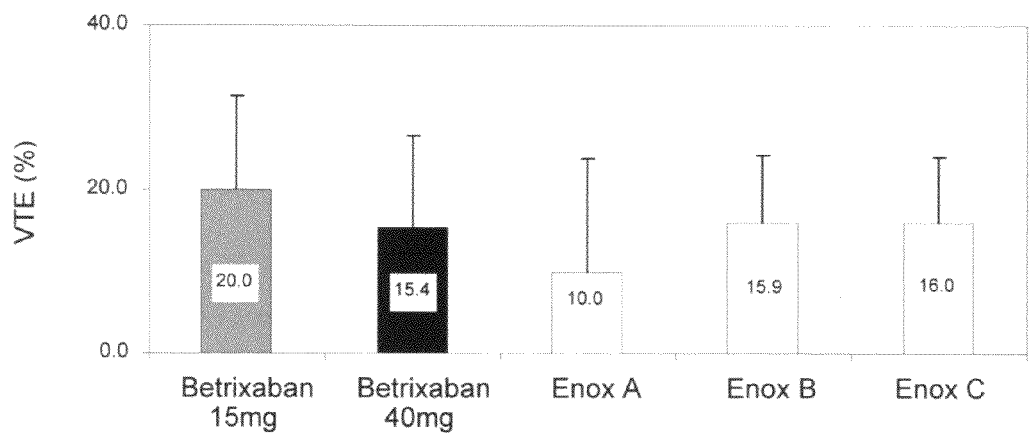
FIG. 6 shows the percentage of patients with venous thromboembolism (VTE) and 95% confidence intervals for betrixaban and enoxaparin as determined by the study in Example 9 with unilateral venography between Days 10 and 14 and for enoxaparin historical controls (B and C) from studies using bilateral venography performed between Days 10 and 14 post orthopedic surgery (total knee replacement). This is more thoroughly discussed in Example 9. The details of the study corresponding to Enox B are reported in *Blood* 102 (11); 2003. The details of the study corresponding to Enox C are reported in the reference by Lassen et al. (*J. Thromb. Haemostasis* 2007 Sep. 15).
Figure 7:
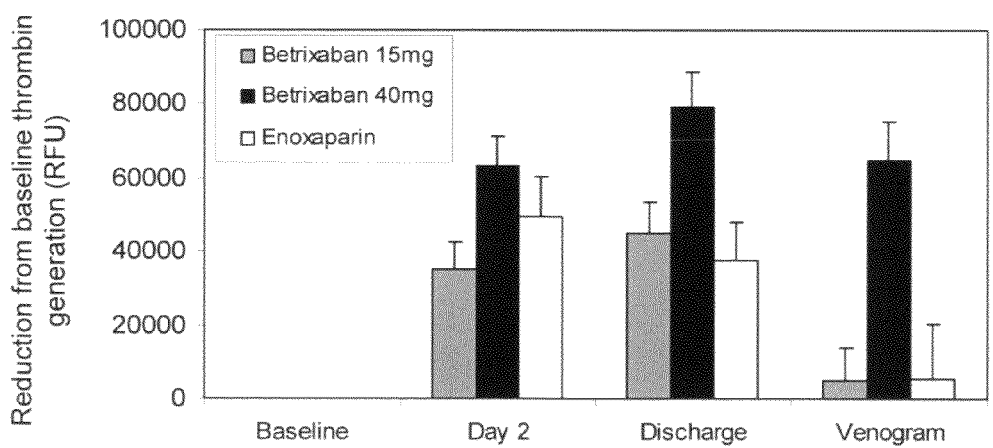
FIG. 7 shows the reduction from baseline thrombin generation upon treatment with varying doses of betrixaban and enoxaparin at day 2, discharge and the venogram. Mean change from baseline relative fluorescence units (±standard error of the mean) in plasma thrombin generation, by visit and treatment is shown. Patients discharged on Day 2 are also represented in the average value for that study day.
Figure 8:
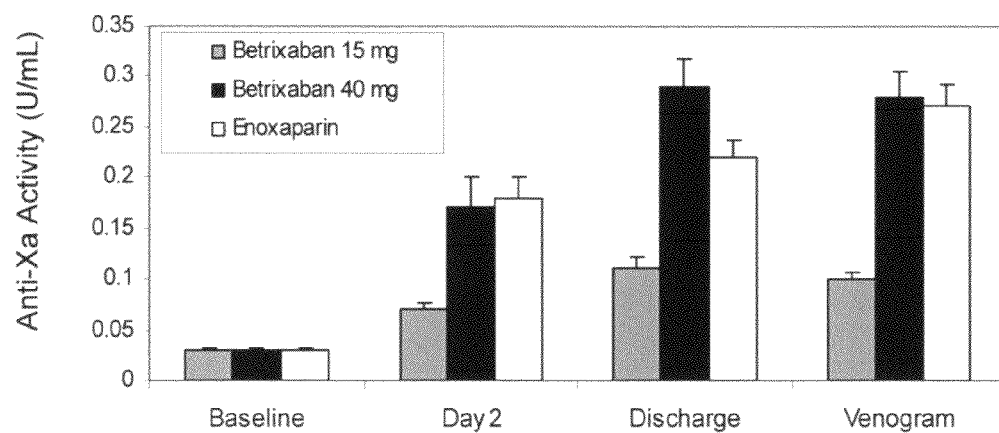
FIG. 8 shows the changes in anti-fXa activity of the varying doses of betrixaban and enoxaparin at day 2, discharge and the venogram. Mean (±standard error of the mean) anti-fXa activity (U/mL), as measured by Coatest LMW heparin assay, by visit and treatment is shown. The detectable limit for anti fXa was 0.05 U/mL; values below the detectable limit were set to 0.025. Patients discharged on Day 2 are also represented in the average value for that study day.
Figure 9:
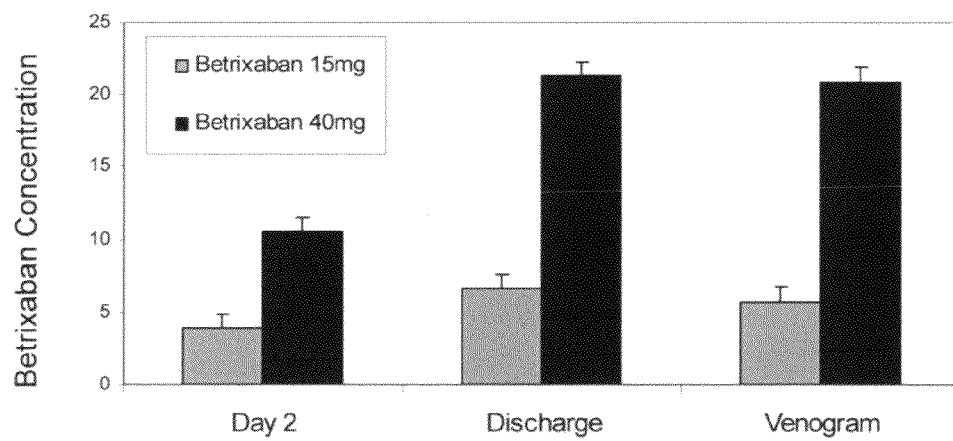
FIG. 9 shows the betrixaban concentration in plasma (ng/mL) of the varying doses of betrixaban at day 2, discharge and the venogram.

FIG. 6 shows the VTE rates and 95% confidence intervals for betrixaban and enoxaparin as determined in this study with unilateral venography between Days 8 and 10 and for enoxaparin historical controls from studies using vilateral venography performed between Days 10 and 14 post-TKR. FIG. 9 depicts plasma betrixaban concentrations after the second dose (Day 2), on discharge and at the time of venography. As expected given the long half-life of betrixaban, mean drug concentrations increased after the first few doses and appeared to reach steady-state by discharge (median Day 4) for both betrixaban dose groups. Betrixaban exhibited a dose-dependent and concentration-dependent effect on inhibition of thrombin generation and anti-Xa levels (FIGS. 7 and 8). The effect of betrixaban 15 mg on the inhibition of thrombin generation was similar to that observed with enoxaparin whereas the effect seen with betrixaban 40 mg was more pronounced. Conversely, the effect seen on anti-Xa activity was similar for betrixaban 40 mg and enoxaparin and less with betrixaban 15 mg. Treatment with betrixaban did not appreciably affect other coagulation parameters (i.e. aPTT, PT and INR).

Betrixaban was effective in preventing VTE after TKR and was safe and well tolerated.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

The invention claimed is:

1. A method of inhibiting coagulation in a human patient in need thereof, comprising administering to the patient once a day, a coagulation inhibiting amount of a compound of Formula II:

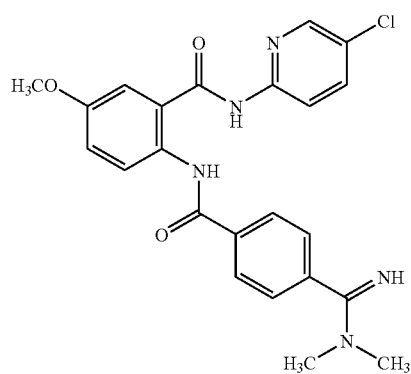

or a pharmaceutically acceptable salt thereof, wherein the coagulation inhibiting amount of the compound is between about 0.4 and about 1.2 mg/kg.

2. The method of claim 1, wherein the pharmaceutically acceptable salt of the compound is a maleate salt.

3. A unit dose formulation comprising a pharmaceutically acceptable carrier and a daily amount of a compound of Formula II:

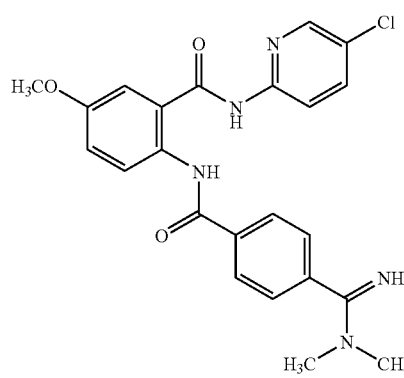

or a pharmaceutically acceptable salt thereof, wherein the daily amount of the compound is between about 30 and 80 mg, and wherein the unit dose formulation is for inhibiting coagulation in a human patient.

4. The unit dose formulation of claim 3, wherein the daily amount of the compound is 30 mg.

5. The unit dose formulation of claim 3, wherein the daily amount of the compound is 80 mg.

* * * * *

UNITED STATES PATENT AND TRADEMARK OFFICE
CERTIFICATE OF CORRECTION

| | | |
|---|---|---|
| PATENT NO. | : 8,404,724 B2 | Page 1 of 1 |
| APPLICATION NO. | : 11/999957 | |
| DATED | : March 26, 2013 | |
| INVENTOR(S) | : Uma Sinha et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1208 days.

Signed and Sealed this
Second Day of December, 2014

Michelle K. Lee
*Deputy Director of the United States Patent and Trademark Office*